(12) United States Patent
Greenberg et al.

(10) Patent No.: US 9,164,062 B2
(45) Date of Patent: Oct. 20, 2015

(54) ANALYZING ULTRASONIC SIGNALS USING A DYNAMIC WINDOW FOR AN EARLY DETECTION OF SCALING IN WATER PROCESSING EQUIPMENT

(75) Inventors: Alan R Greenberg, Boulder, CO (US); Jack Gilron, Beer Sheva (IL); Keith D Cobry, Lafayette, CO (US); Elmira Kujundzic, Erie, CO (US); Xiao Yun Lu, Longmont, CO (US); Guy Mizrahi, Beer Sheva (IL); Michael Peterson, Orono, ME (US)

(73) Assignees: THE REGENTS OF THE UNIVERSITY OF COLORADO, A BODY CORPORATE, Denver, CO (US); BEN-GURION UNIVERSITY OF THE NEGEV RESEARCH AND DEVELOPMENT AUTHORITY, Beer-Sheva (IL)

( * ) Notice: Subject to any disclaimer, the term of this patent is extended or adjusted under 35 U.S.C. 154(b) by 455 days.

(21) Appl. No.: 13/809,780
(22) PCT Filed: Jul. 12, 2011
(86) PCT No.: PCT/IB2011/053115
§ 371 (c)(1),
(2), (4) Date: May 28, 2013
(87) PCT Pub. No.: WO2012/007909
PCT Pub. Date: Jan. 19, 2012

(65) Prior Publication Data
US 2013/0238133 A1    Sep. 12, 2013

Related U.S. Application Data

(60) Provisional application No. 61/363,305, filed on Jul. 12, 2010.

(51) Int. Cl.
*G01N 29/02* (2006.01)
*G01N 29/032* (2006.01)

(52) U.S. Cl.
CPC .............. *G01N 29/02* (2013.01); *G01N 29/032* (2013.01); *G01N 2291/0258* (2013.01); *G01N 2291/02491* (2013.01); *G01N 2291/02836* (2013.01); *G01N 2291/2634* (2013.01)

(58) Field of Classification Search
CPC .................. G01N 29/032; G01N 2291/02491; G01N 2291/2634; G01N 29/02; G01N 2291/02836; G01N 2291/0258
USPC ................................. 73/599; 700/266; 702/25
See application file for complete search history.

(56) References Cited

U.S. PATENT DOCUMENTS

2004/0016699 A1 * 1/2004 Bayevsky ..................... 210/636
2006/0287836 A1   12/2006 Mateo et al.
(Continued)

FOREIGN PATENT DOCUMENTS

WO    WO 00/04987    2/2000
WO    WO2006116533    * 11/2006

OTHER PUBLICATIONS

Lalot, "On-line detection of fouling in a water circulating temperature controller (WCTC) used in injection moulding", Applied Thermal Engineering, vol. 26, Aug. 1, 2006, pp. 1087-1094.

(Continued)

Primary Examiner — J M Saint Surin
(74) Attorney, Agent, or Firm — Nixon & Vanderhye P.C.

(57) ABSTRACT

A method of early detection of scaling on internal surfaces of conduits of water processing equipment, is provided herein. The method includes: transmitting ultrasonic signals through the wall of the conduits; deriving data samples from received ultrasonic signals or reflections thereof; calculating a moving average of the scatter of the ultrasonic signals, over time, based on the data samples; applying a statistical operand to the moving average, to yield a statistical distribution metric; determining a dynamic window defined by: (i) an upper boundary being the moving average plus at least a fraction of the statistical distribution metric and (ii) a lower boundary being the moving average minus the at least a fraction of the statistical distribution metric; generating a trend line being a smooth fitting of the derived samples; and monitoring the trend line within the window to detect a crossover of the trend line at either of the boundaries.

28 Claims, 16 Drawing Sheets

(56) References Cited

U.S. PATENT DOCUMENTS

2009/0266762 A1* 10/2009 Ito et al. .......... 210/636
2011/0186513 A1* 8/2011 Vuong et al. .......... 210/636
2012/0145633 A1* 6/2012 Polizzotti et al. .......... 210/652

OTHER PUBLICATIONS

International Search Report for PCT/IB2011/053115, mailed Feb. 2, 2012.
Written Opinion of the International Searching Authority for PCT/IB2011/053115, mailed Feb. 2, 2012.
Mairal, A.P. et al., Real-time measurement of inorganic fouling of RO desalination membranes using ultrasonic time-doma in reflectometry, Journal of Membrane Science, vol. 159, No. 1-2, (Jul. 1, 1999), pp. 185-186.
Mairal, A.P. et al., "Investigation of membrane fouling and cleaning using ultrasonic time-domain reflectometry", Desalination, vol. 130, No. 1, (Sep. 1, 2000), pp. 45-60.
Hunter, J., "The Exponentially Weighted Moving Average", Journal of Quality Technology, vol. 18, No. 4, (Oct. 1, 1986), pp. 203-210.

* cited by examiner

ANALYZING ULTRASONIC SIGNALS USING A DYNAMIC WINDOW FOR AN EARLY DETECTION OF SCALING IN WATER PROCESSING EQUIPMENT

This application is the U.S. national phase of International Application No. PCT/IB2011/053115, filed 12 Jul. 2011, which designated the U.S. and claims the benefit of U.S. Provisional Application No. 61/363,305, filed 12 Jul. 2010, the entire contents of each of which are hereby incorporated by reference.

BACKGROUND

1. Technical Field

The present invention relates to water processing systems and more particularly, to an early detection of scaling processes in such systems, using statistical methods.

2. Discussion of the Related Art

There are many water treatment processes involving the flow of aqueous streams in opaque conduits wherein scaling of internal structures of said conduits will cause damage to the process or increase the resources needed to carry out such processes. Examples of such conduits with internal structures are heat exchangers containing heat transfer surfaces and pressure vessels containing membrane elements for water treatment.

The scaling referred to herein is the precipitation of sparingly soluble salts (including but not limited to sulfates of calcium, barium and strontium, calcium carbonate, silica and calcium fluoride) on the internal surfaces of these conduits due to the creation of supersaturation conditions on these internal surfaces by temperature or concentration gradients. By the time that the effects of such scaling are detected from process parameters such as from changes in temperature decreases or higher heating or cooling duties in a heat exchanger, or from product water flux-decline or increased applied pressure in membranes, irreversible damage could be caused to the equipment. At the least it could require costly downtime to repair the equipment. If there were an early warning system that would allow treating the equipment with preventative steps, it could be possible to keep the equipment operating without costly downtime or damage.

Because sparingly soluble salts usually have an induction time between the time that supersaturated conditions are obtained and the time that scaling of internal surfaces begins, one can take preventive actions just before, or at the end, of such an induction time by a variety of approaches. One example is the use of osmotic flushing to periodically sweep away supersaturated solutions and other foulants in reverse osmosis (RO) processes. Another example is the use of blowdown in cooling towers and flushing of heat exchangers with undersaturated solutions. Another solution is the use of flow reversal to replace supersaturated concentrate solution with undersaturated feed solution next to a desalination membrane. The problem is that if the early warning is too early and sensitive, then the preventative treatment sequence can be too frequent resulting in unnecessary use of chemicals, loss of production, or wear of equipment.

Because the equipment is inside an opaque conduit, it is not possible to visually inspect the equipment in real time during operation to determine when scaling occurs. One approach to overcoming the lack of optical transparency is to use an external device placed downstream of the equipment that is at risk to scaling and then optical units can be used to observe the onset of scaling. A similar known device monitors the flux decline in an external device downstream of the pressure housings containing membrane desalination modules. The disadvantage of such devices is that they are unable to exactly reproduce the conditions in the equipment in terms of flow patterns and supersaturation conditions, and can be either too sensitive (if they generate greater supersaturation than the actual equipment) or not sensitive enough (if they generate less local supesaturation than the actual equipment).

Another option is to use devices that do allow sampling of the conditions of the internal surfaces of an opaque conduit containing water processing equipment. A well known example is the use of ultrasound, which is used for detecting defects in welding in pipes and leaks inside conduits in the chemical-processing industry. A known method detects the presence of mineral deposits on water treatment membrane surfaces in both opaque flat sheet and commercial spiral wound pressure vessels. However, the methodology involved collecting the data and then analyzing the complex waveforms generated offline due to the extensive analysis required. While this approach was effective as a diagnostic, it was not effective as an on-site early warning device that could be used for triggering process changes and preventive steps in real time. Part of the reason for this, is that enough time must pass for the signal to significantly deviate from the background signal and by direct inspection this often requires so much time that scaling has already proceeded to a much greater extent. Therefore this becomes a problem of statistically identifying a signal deviating from background noise.

BRIEF SUMMARY

The present invention, in embodiments thereof, overcomes the drawbacks of the prior art by providing a method of detecting pre-conditions of scaling, potentially occurring in conduits of water processing equipment. Non limiting examples for such water processing equipment may include reverse osmosis, nanofiltration, ultrafiltration membranes, heat exchangers, and water transport pipelines. The method includes the following stages: transmitting ultrasonic signals through the conduits; deriving data samples from received ultrasonic signals or reflections thereof; calculating a moving average of the scatter of the ultrasonic signals, over time, based on the data samples; applying a statistical operand to the moving average, to yield a statistical distribution metric; determining a dynamic window defined by: (i) an upper boundary being the moving average plus at least a fraction of the statistical distribution metric and (ii) a lower boundary being the moving average minus the at least a fraction of the statistical distribution metric; generating a trend line being a fitting of the derived samples; and monitoring the trend line within the dynamic window to detect a crossover of the trend line at either of the boundaries.

Another aspect of the invention provides a system for detecting pre-conditions of scaling occurring on internal surfaces of conduits of water processing equipment. The system includes one or more ultrasonic transceivers that may each include a transmitter and a receiver. The transceivers are configured to transmit one or more ultrasonic signals through the walls of the conduits, and receive the ultrasonic signals and/or reflections thereof.

The system further includes a sampler configured to sample in real-time, data samples indicative of spectral parameters, from received ultrasonic signals or reflections thereof. The system further includes a processing unit, possibly implemented as a computer. The processing unit is configured to:

(i) calculate a moving average of a scatter of the ultrasonic signals, over a specified period of time, based on the data samples;

(ii) apply a statistical operand to the moving average, to yield a statistical distribution metric;

(iii) determine a dynamic window defined by: (i) an upper boundary being the moving average plus at least a fraction of the statistical distribution metric and (ii) a lower boundary being the moving average minus the at least a fraction of the statistical distribution metric;

(iv) generating a trend line, preferably but not necessarily, smooth fitting of the derived samples; and (v) monitor the trend line within the dynamic window to detect a crossover of the trend line at the upper boundary or the lower boundary.

In some embodiments, the system may further include a control module configured to issue an alert upon the detection of a crossover. In other embodiments, the control unit may further be configured to apply an intervention to the water processing equipment such that the scaling is avoided. Non-limiting examples for such an intervention may include: flow reversal, flushing with undersaturated water, osmotic flushing, and a use of a chemical cleaning solution.

These, additional, and/or other aspects and/or advantages of the embodiments of the present invention are set forth in the detailed description which follows; possibly inferable from the detailed description; and/or learnable by practice of the embodiments of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings.

Figure 1:
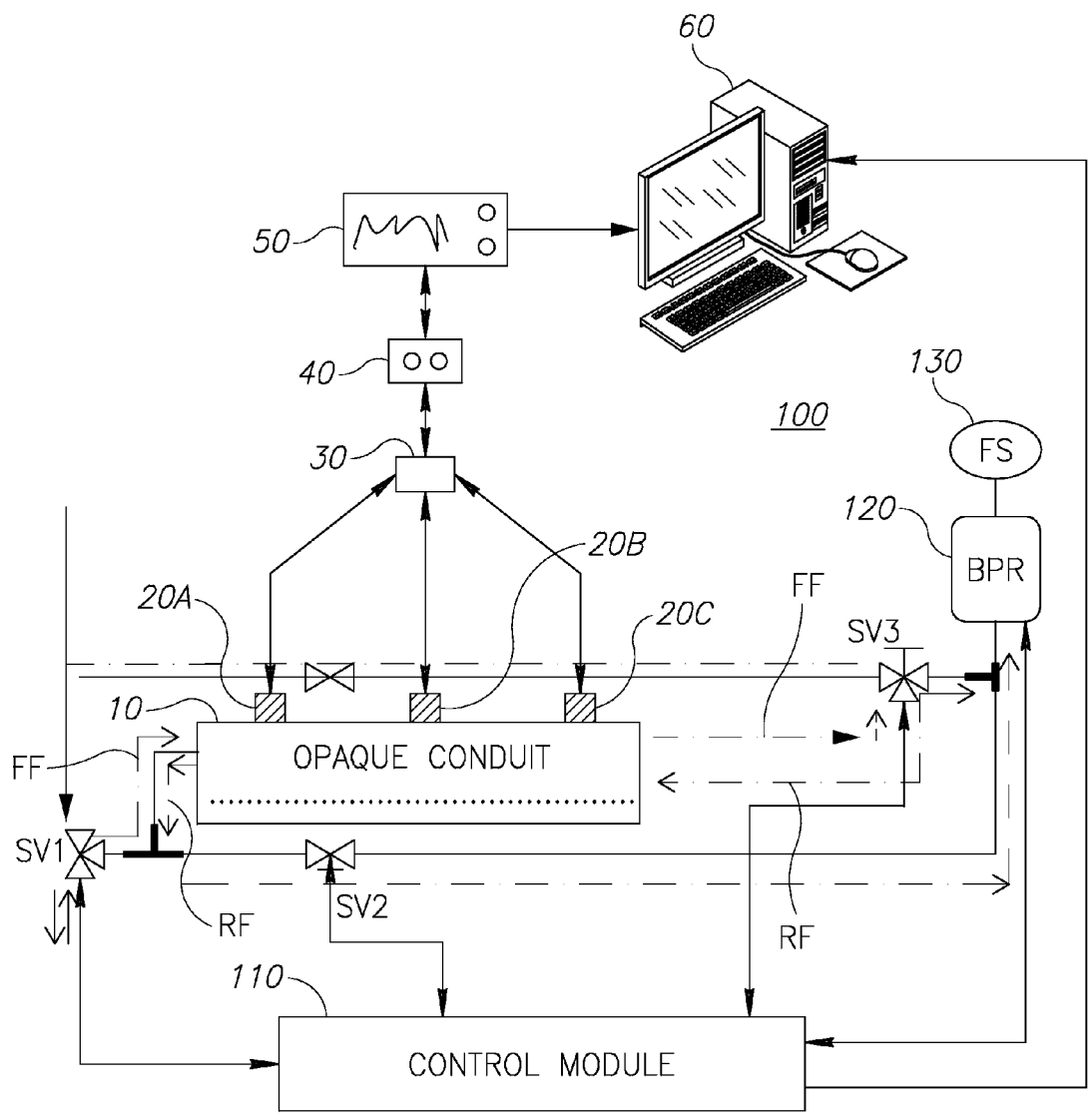
FIG. 1 is a block diagram illustrating a system according to some embodiments of the invention.

The drawings together with the following detailed description make apparent to those skilled in the art how the invention may be embodied in practice.

DETAILED DESCRIPTION

Prior to setting forth the detailed description, it may be helpful to set forth definitions of certain terms that will be used hereinafter.

The term "scaling" as used herein in this application refers to the accumulation of unwanted materials on solid surfaces, most often in an aquatic environment. In scaling, the unwanted materials usually include non-living inorganic substances such as calcium sulfate and calcium carbonate. Scaling is usually distinguished from other surface-growth phenomena in that it occurs on a surface of a component, system or plant performing a defined and useful function, and that the scaling process impedes or interferes with this function.

The term "ultrasonic transceivers" as used herein in this application refers to components which have both transmitting and receiving functionality of ultrasonic signals. It is understood that other embodiments of the present invention may be implemented with the transmitting and the receiving functionality in a separated configuration of transmitter and receiver.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

FIG. 1 illustrates a non-limiting exemplary system 100 according to some embodiments of the present invention. System 100 includes: an opaque conduit 10 through which a potentially supersaturated aqueous stream is pumped, control elements (switching valves—SV1, SV2, SV3 and back-pressure regulator (BPR) 120 comprising a flow sensor (FS) 130 for determining what kinds of fluid and under what conditions they are pumped through the opaque conduit, a control module 110 implemented by a programmable logic controller (PLC), a microprocessor, relays, and the like configured to change the state of the control elements to effect the change in flow conditions or fluid identity flowing through opaque conduit 10, an early-warning system comprising ultrasonic transducers 20A-20C for producing wave signals capable of passing through the walls of opaque conduit 10, a multiplexer 30, a pulser-receiver 40, an oscilloscope 50 or other device suitable for rapid acquisition (sampling and storing) of wave signals reflected from (or transmitted through) the walls of opaque conduit 10, and data processing unit 60 (such as a computer) for processing the spectra of the acquired wave signals in real time and for following the trend of the processed wave signal over time.

Data processing unit 60 is configured to carry out the following actions:

Real-time analysis of acquired wave signals to obtain a characteristic property of the transmitted or reflected wave spectrum. The characteristic properties may include: amplitude, variance between emitted and reflected/transmitted wave, characteristic frequency shift of Fourier transform, a combination of such characteristics, as well as derived properties such as the difference between maximum and minimum amplitude and the like;

Real-time statistical analysis of scatter (e.g. standard deviation or variance) of the accumulated wave signals for the characteristic reflected/transmitted spectrum property from time 0 to time t; in an alternative realization the scatter can be evaluated for reflected or transmitted wave signals that have been collected between a time t and t−Δt where Δt is the duration of the sampling window which is long enough (at least 0.25 h but preferably longer than 0.5 h) to evaluate the characteristic noise of the system;

Determination of a window defined by maximum and minimum values (boundaries) based on the scatter function within which a trend line should stay; these can be some monotonic functions of the standard deviation or variance of the characteristic spectrum property recorded from the accumulated processed wave signals from the start to time t or from time t−Δt to t.

In an additional realization, the window can be defined by the maximum and minimum values of the scatter function based on the characteristics of the first n (at least 10 and preferably at least 30) sampled wave signals covering a time period of 15-300 minutes.

Determination of a trend line (linear or non-linear) that reasonably represents the local characteristic spectrum property over time from t=0 to t or alternatively from t−Δt to t; and issuance of warning indications whenever the trend line intersects with the window boundaries for taking preventive actions to protect the internal surfaces of the conduit. The meaning of intersection can be when the end point of the trend line meets one of the window boundaries or exceeds it by a user-specified amount, either in signal magnitude or in time.

The inherent advantages of this method of processing the reflected or transmitted wave signals are as follows: (1) the simplicity of the method (minimization of necessary calculations) allows analysis to be done in real time, which is required for the control aspects; and (2) the system is robust in that it is sufficiently sensitive to identify scaling but accommodates an appropriate level of system variability without triggering a signal (for example, all experiments conducted have window limits that correspond to a level of standard deviation that is approximately 0.5%-1.5% of the average signal).

Data processing unit 60 sends a signal to control module 110 whenever the processed wave signals exceeds either of the window boundaries. Control module 110 then resets the control elements (e.g. SV1, SV2, SV3 and BPR 120 and associated pumps) to allow change of the flow fluid so that internal surfaces that were exposed to supersaturated solutions are now exposed to undersaturated solutions.

While three transducers are shown in FIG. 1, it is clear that there could be as few as one, and that there could be many more transducers as well. Multiplexer unit 30 may be implemented by any electric or electronic switching element that allows acquisition of more than one input and transmission of more than one output. The pulser-receiver may be implemented by means of any kind of wave-generating and wave-recording equipment that allows the actuating of ultrasonic transducers (or ultrasonic sensors). The ultrasonic transducers may be implemented by any type of piezo-electric-based or magnetostrictive-based transducer that allows the conversion of electric signals to mechanical displacements and vice versa in frequencies ranging from 0.1 MHz to 20 MHz and preferably in the range of 0.5 MHz to 10 MHz. Data collection can be effected by any fast A/D interface and storage unit capable of capturing the wave form such that a complete waveform with the above mentioned frequencies can be sampled at a density of 20 to 1000 points per wave form and preferably at least 100 points per wave form.

Data processing unit 60 may be implemented by means of a microcomputer, PC, microprocessor, microcontroller, DSP processor, or any suitable unit with an onboard mathematics processor allowing statistical evaluation of collected data.

Following are several examples that are based on experimentations carried out by the inventors. The examples are used by way of illustration and not by way of limiting, how embodiments of the present invention are reduced into practice in a real-life environment.

EXAMPLE 1

Figure 2:
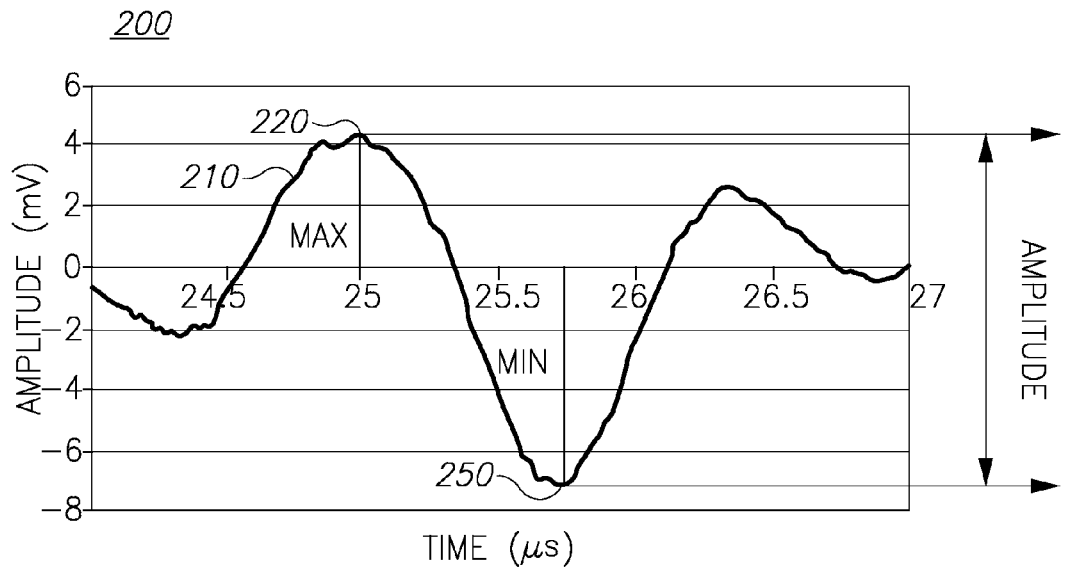
FIG. 2 is a graph illustrating an aspect according to some embodiments of the invention.

In a specific non-limiting embodiment of the invention the processing of the wave signals was carried out as follows:

Real-time acoustic spectra were generated by means of 10 MHz planar ultrasonic sensors using an ultrasonic pulser/receiver in conjunction with a digital storage oscilloscope. A custom-made multi-channel scanner was used for acquiring the wave signals reflected in response to the acoustic spectra emitted from the multiple (3) ultrasonic sensors. A custom LabVIEW program along with a 12-bit multifunction I/O analog-to-digital converter was used to obtain a time-domain ultrasonic wave signal (e.g., sampling rate of about $0.5\text{-}20\times 10^9$ points/s, preferably about $5\times 10^9$ points/s) from each ultrasonic sensor over a time period of 0.2-10 μs every 5 min, preferably 3 μs every 5 min. A representative acoustic time-domain wave signal 210 with its maximum 220 and minimum 250 is shown in FIG. 2. The time-domain signal is plotted as amplitude (mV) versus signal arrival time (μ).

In this example each acoustic time-domain wave signal spectrum (containing 500 data points) was saved as a text file in a plain text editor (Notepad) in Microsoft Windows, and the data points were then copied into a commercially-available statistical analysis program Minitab (Minitab Inc.). The maximum and minimum values from of each time-domain ultrasonic wave signal acquired (500 data points) were then extracted using the "Basis statistics" tool option in the Minitab software, and copied into a Microsoft Excel spreadsheet. The difference between the maximum and minimum values (MAX subtracted from MIN) is defined as the amplitude (AMPLITUDE) of the time-domain wave signal. The calculated amplitudes (mV) of the time-domain ultrasonic wave signals were then plotted as a function of time (min).

A "dynamic window" for each flow cycle is preferably obtained using the mean amplitude value with boundaries that include the upper (sum of the mean amplitude value and the standard deviation) and the lower (standard deviation subtracted from the mean amplitude value) limit. The mean amplitude ($\bar{x}$) may be calculated using equation (1) and the standard deviation ($\sigma$) may be calculated using equation (2):

$$\bar{x} = \frac{1}{n}\sum_{i=1}^{n} x_i \quad (1)$$

$$\sigma = \sqrt{\frac{1}{n}\sum_{i=1}^{n}(x_i - \bar{x})^2} \quad (2)$$

The instantaneous mean and standard deviation values can be successively calculated by adding any new calculated amplitude value and recalculating the mean and standard deviation values. In this manner, the limits of the "dynamic window" are continuously updated. Using the "Add trend line" function in Microsoft Excel, a second-order polynomial regression was used to fit a trend line to these data.

Figure 3:
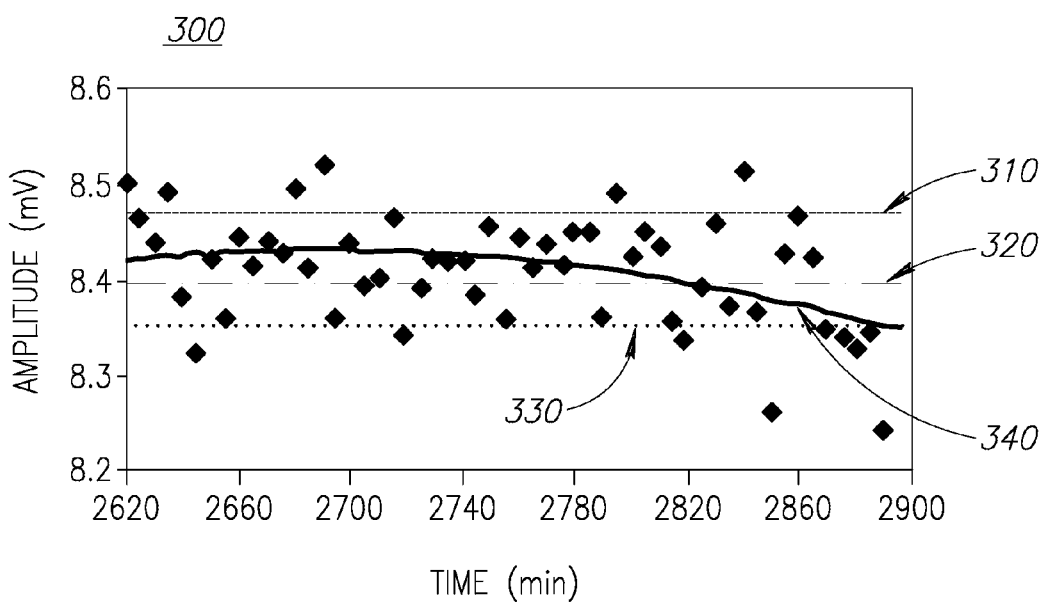
FIG. 3 is a graph illustrating an aspect according to some embodiments of the invention.

The same trend line could be developed using other commercial math packages such as Polymath or Matlab or code could be written in any high level or machine language without taking away from the generality of the approach. For example, a custom Matlab program has been developed and used to automatically plot acoustic amplitude data in real time. This program then generates a "dynamic window" with boundaries (as explained hereinabove) as well as a trend line based upon a second-order polynomial regression of the amplitude with the experimental run time. When the trend line reaches either the upper or lower window boundary, a "crossover" or "breakthrough" is identified. A representative "dynamic window" is presented in FIG. 3 in which graph 300 shows an average value 320 an upper boundary 310, a lower boundary 330, and a trend line 340. The following variations of this scheme for defining the breakthrough are defined below and illustrated in FIG. 4 in which 410A-C represent the upper boundary, 430A-C represent the lower boundary, 420A-C represent the average, and 450A-C represent the trend line as follows:

The change in flow direction was triggered after a departure of the trend line from the dynamic window and confirmation by three subsequent contiguous ultrasonic data points that also were outside of the window boundary ("multiple departure" switch) (400A). The change in flow direction was triggered immediately once the trend line was out of the dynamic window boundary ("first departure" switch) (400C). A dynamic window that used only the initial portion of the cycle and a trend line based upon ultrasonic points in the final portion cycle ("modified first departure" switch): here only the first 30 amplitude points were used to constitute the window boundaries that remained unchanged over the duration of the test, while the trend line was formed using only the 30 last amplitude points of the current cycle (400B). All of these are particular embodiments of algorithm of the claimed invention without exhausting its generality as presented in the general description above.

Figure 5:
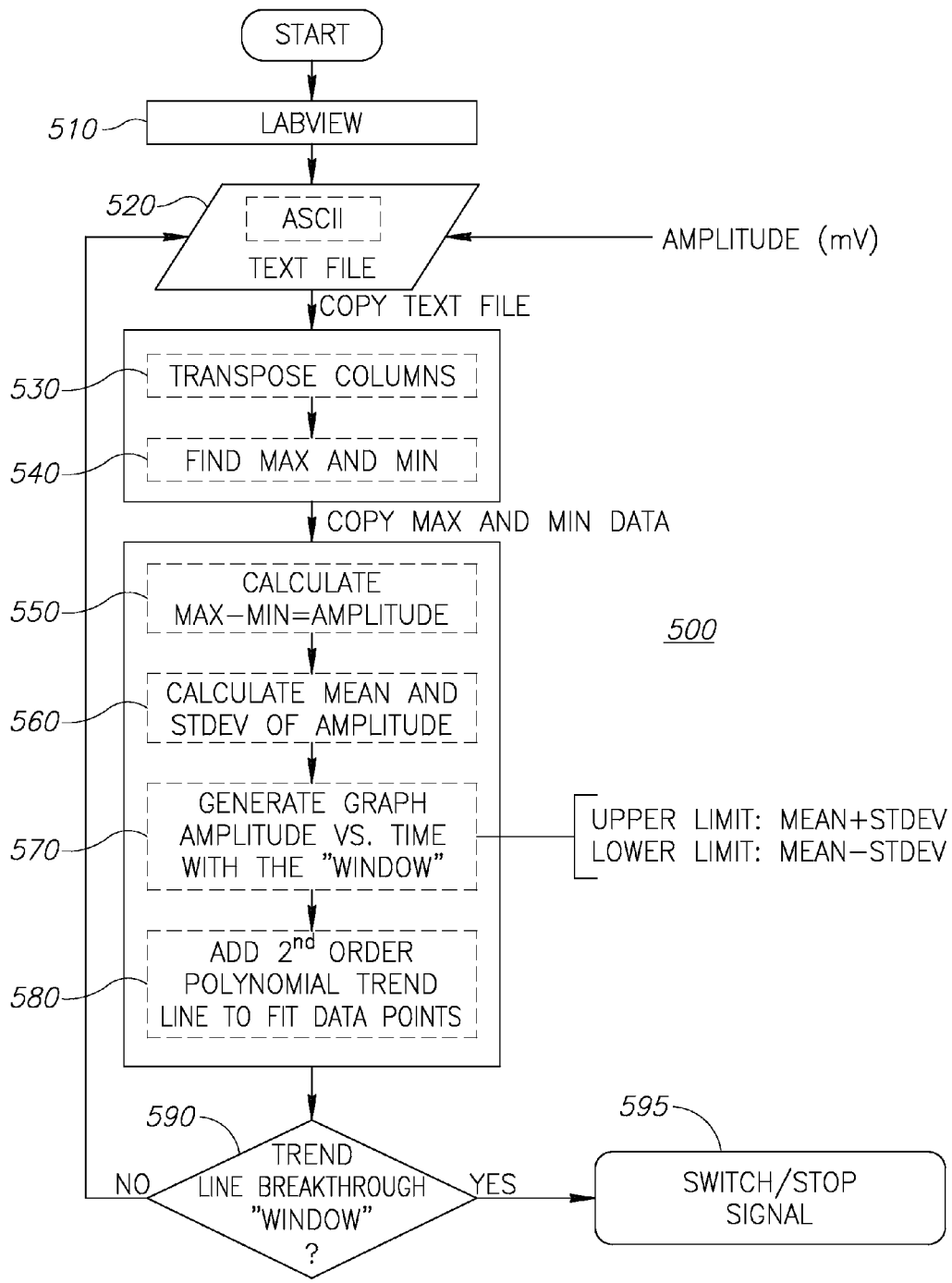
FIG. 5 is a high level flowchart illustrating a method according to some embodiments of the invention.

A flowchart illustrating the steps in acquiring and processing the time-domain ultrasonic wave signals and executing the algorithm is shown in FIG. 5. The method starts off by using LabVIEW software 510; data are being acquired and converted into a text file 520. Columns are transposed 530 and maximum and minimum are determined 540 from which amplitude is calculated 550 and then mean and standard deviation are also calculated 560. A graph is generated with a dynamic window over time 570 on which a trendline being a $2^{nd}$ order polynomial fitting is added 580. Then, upon breakthrough detection 590 a signal is given for intervention or the process is stopped 595.

Figure 6:
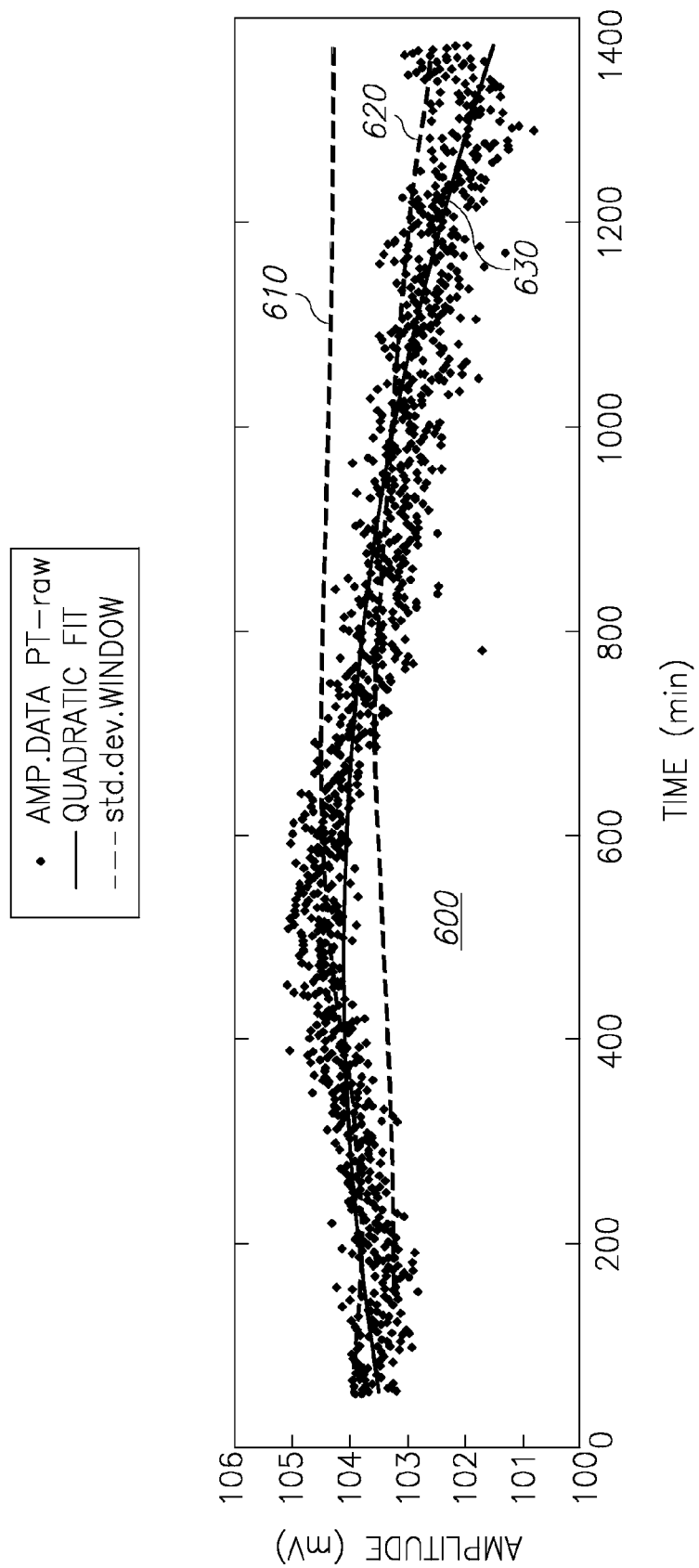
FIG. 6 is a graph illustrating an aspect according to some embodiments of the invention.
Figure 7:
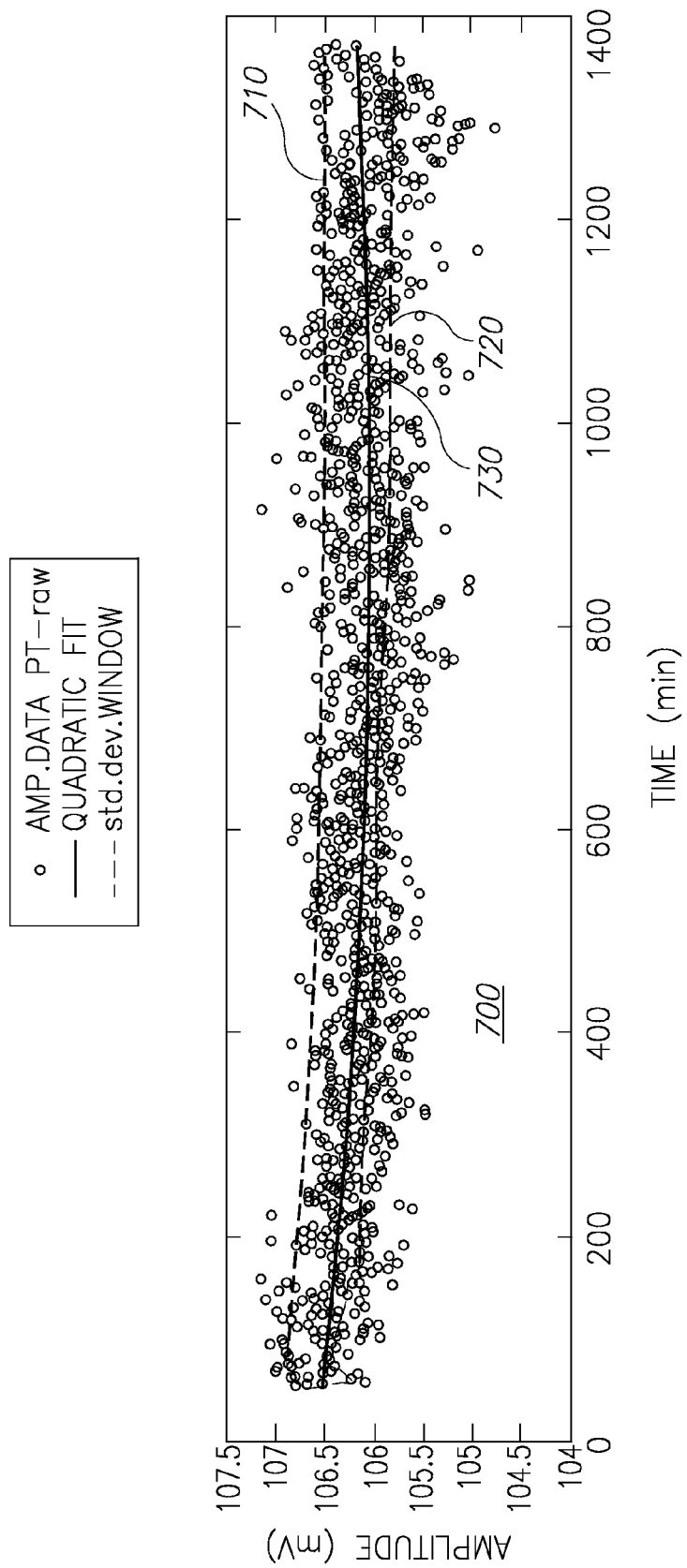
FIG. 7 is a graph illustrating an aspect according to some embodiments of the invention.

In an industrial environment the temperature of the environment can cause changes to the signal that could be misinterpreted as arising from a scaling event. Such a phenomenon is illustrated in FIG. 6. As shown in graph 600, There is a lag time=$\Delta$ between the change in temperature and the change in the signal characteristics related to the time it takes the surrounding temperature to affect the temperature of the coupling fluid between the ultrasonic transducer and the top plate of the flow cell.

This can be avoided by one skilled in the art by either placing the transducers in a locally controlled temperature environment or by applying a temperature correction to the ultrasonic signal.

Alternatively, a thermocouple or similar device may be used to continuously monitor temperature and apply an appropriate input to the program. It should be noted that the ambient temperature effects should not be confused with temperature effects due to the change in the temperature of the fluid in the system—this must also be monitored and independent corrections applied if necessary.

The temperature correction is of the form:

$$[A(t)]\text{corr}=a*T(t-\Delta)+A(t) \quad (3)$$

where A is the total amplitude difference of the wave form, t refers to the time at which the signal was recorded and $T(t-\Delta)$ is the temperature at a time $t-\Delta$ before the signal A(t) was recorded at time t. When this is done one obtains a stable signal (see FIG. 8).

A comprehensive set of experiments using the algorithm as summarized in FIG. 5, consistently indicated that "breakthrough" was related to membrane scaling. The "breakthrough" provides a "switch" signal. This is a signal to take preventative steps to protect the membrane from significant scaling. In the examples that follow, the signal is used to reverse the flow direction in the module.

Figure 8:
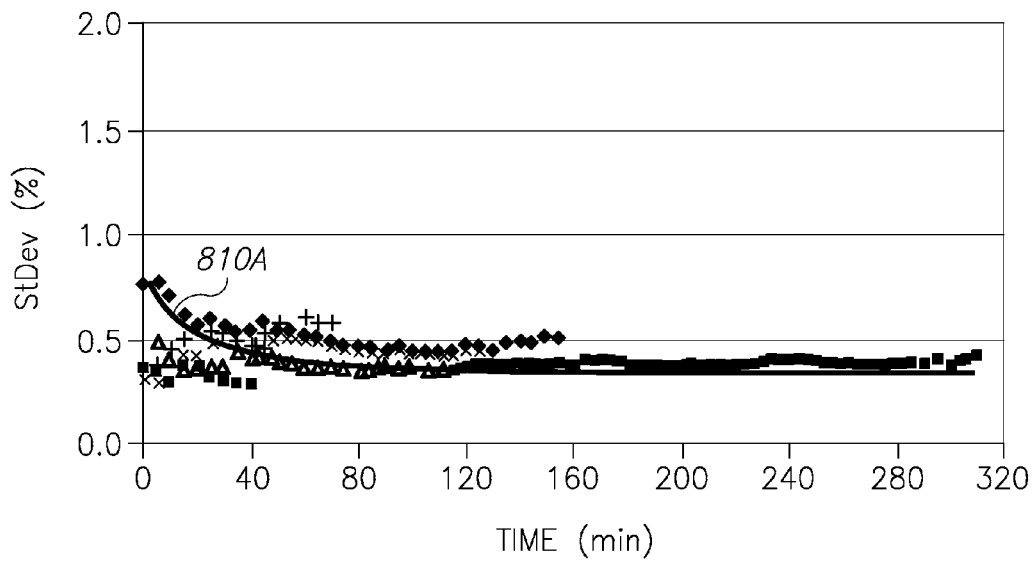
FIG. 8 shows two graphs illustrating an aspect according to some embodiments of the invention.
Figure 8:
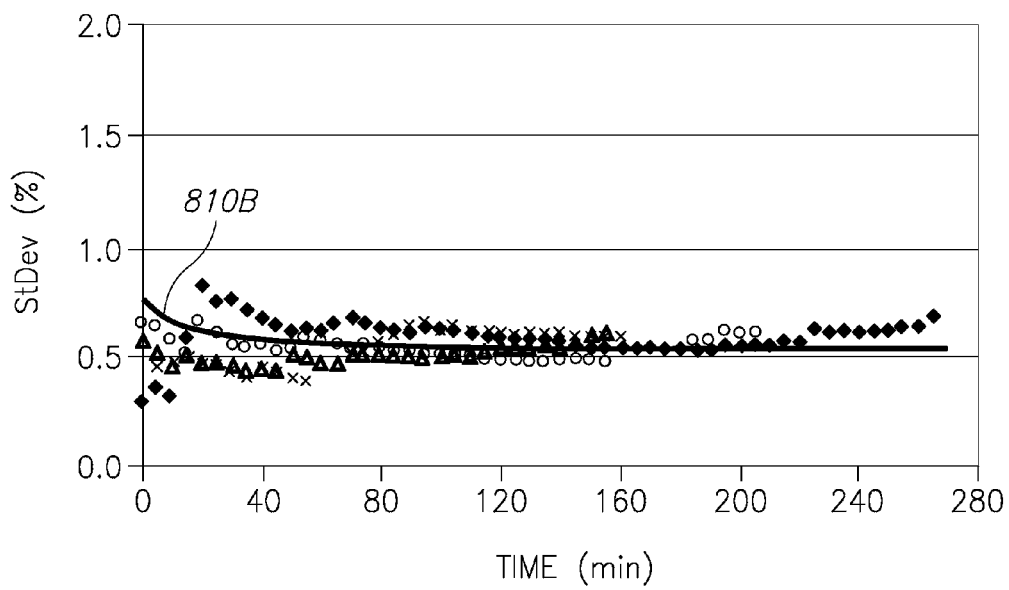

It is noted that the scaling incubation time is defined as the time interval between the cycle start and the "switch" signal. This approach assumes only that the incubation time for scaling is long enough to establish a representative "window" since an incubation time based on too few data samples would potentially be unreliable. Plots showing the cumulative standard deviation (%) for various experiments as a function of time (min) are shown in FIG. 8. FIG. 8 presents data for sensor C in the first forward-flow cycle (800A) and sensor A in the first reverse-flow cycle (800B). Standard deviation is calculated as the percentage of the mean amplitude. Results show a very small spread of average amplitude data (standard deviation is <1%). The data from a range of experiments follow an overall trend in which the standard deviation for the sensors in each flow cycle approaches an asymptotic value after an initial decrease. The findings suggest that a minimum number of data points (or a minimum time) is necessary to establish lower and upper boundaries and a relatively constant value for the limits of the "dynamic window". For these experiments, the minimum number of data points is ~10 which correspond to ~50 min of module operation if the sampling time is every 5 minutes.

While a dynamic window and corresponding trend line are obtained from each ultrasonic sensor, the incubation time is determined only from the governing ultrasonic sensor which samples the membrane where supersaturation will be highest. It should be further noted that it may prove advantageous to use signals from a sensor not at the most downstream position to best control the flow reversal. In the case of a flow-reversal setup this will be the downstream sensor which is (C) in the forward-flow direction and the (original) upstream sensor (A) in the reverse-flow direction. In addition, in order to determine the appropriate time to switch the flow direction, the switch signal can also be used to terminate the experiment to study early-stage scaling.

In the current methodology a second-order polynomial regression line was applied to fit the experimental data points, but trend lines using other linear or non-linear fitting equations could also be used. In addition, a more sensitive response to the onset of scaling could be obtained via adjustment of the upper and lower window boundaries, i.e., instead of using one standard deviation of the mean of acoustic data amplitude, a fractional value could be used. For example, use of a 95% (or less) of the standard deviation would enable a selected trend line to breakthrough the "dynamic window" earlier in time. Correspondingly, a value larger than the standard deviation would enable to a selected trend line to breakthrough the "dynamic window" later in time. Thus, judicious selection of the data processing parameters would enable an optimum switch strategy to be employed whereby either a more conservative (fewer false positives) or a less conservative (more switches) could be utilized.

In summary, this novel methodology is simple to employ, gives reliable results and incorporates an appropriate balance between sensitivity and "false-positive" responses. This novel methodology was used here for the first time to successfully control flow reversal in a series of systematic and comprehensive reverse osmosis desalination experiments.

Figure 9:
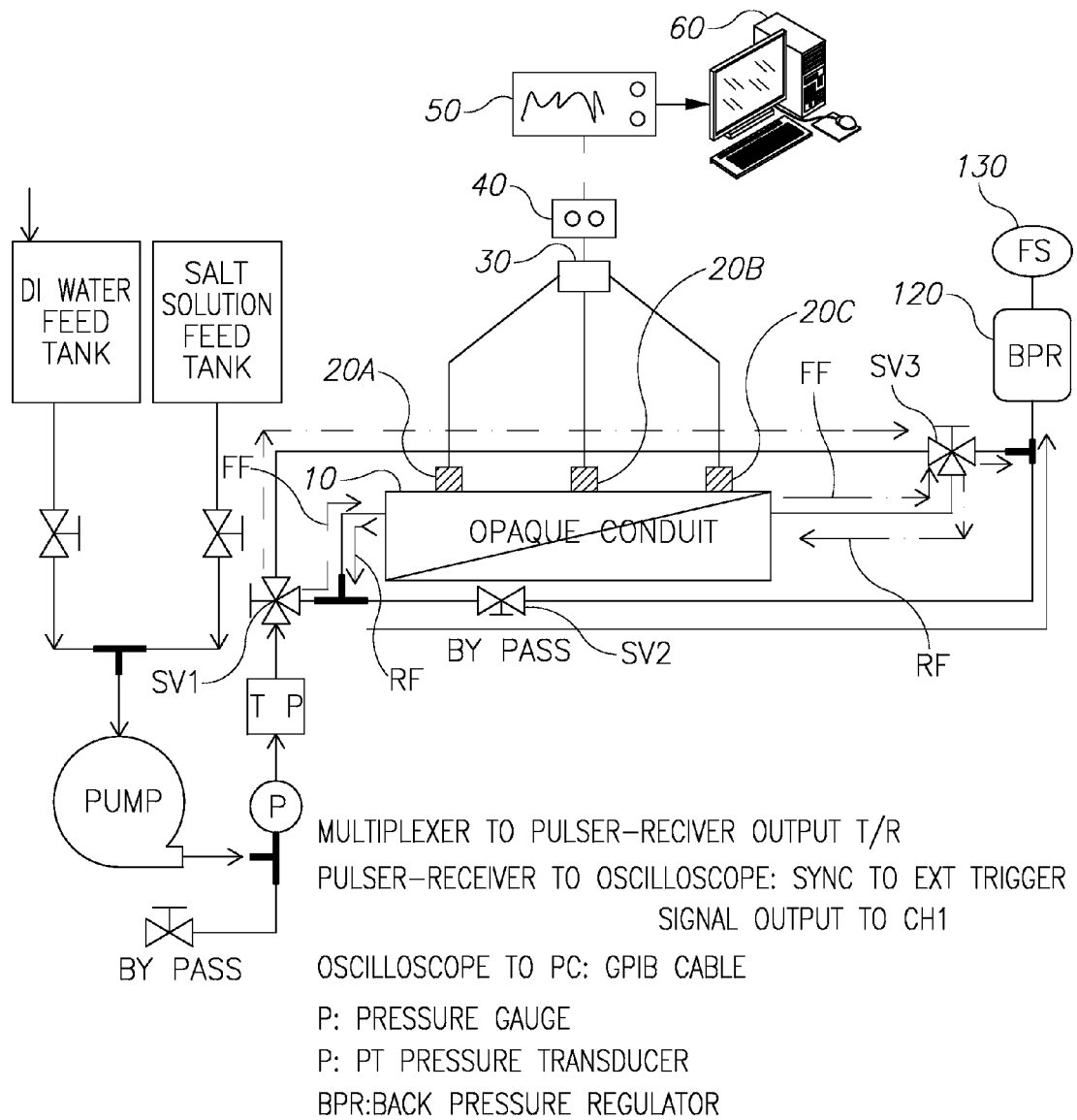
FIG. 9 is a block diagram illustrating another aspect according to some embodiments of the invention.
Figure 9:
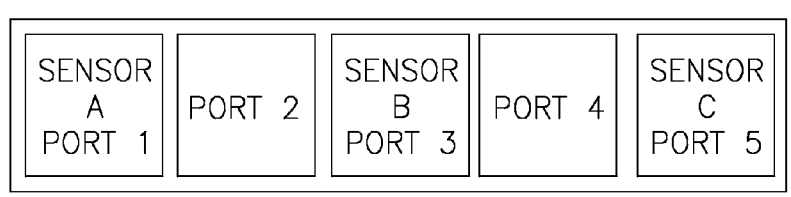

A schematic illustration of the bench-scale RO system used for evaluating the effectiveness of the ultrasonic early warning system is presented in FIG. 9. This RO system utilizes two 10-L plastic tanks containing aqueous solutions: one tank contains dionized (DI) water and other contains the salt solution feed. The feed tank solution is stirred continuously with a magnetic stir bar. The feed solution temperature is controlled at 23±1° C. using an in-line coiled stainless steel heat exchanger connected to a chiller (model 9101, Fisher Scientific), and measured with a digital thermometer (model 217GA, Omega). An in-line filter (model PL-U.1×10UL, 0.1-μm, Serfilco) is installed to eliminate particulate in the bulk flow to the membrane. A booster pump (model 7131-1007, Little Giant Pump Co.) is placed before the in-line filter to eliminate possible cavitation in the high pressure pump. The feed solution is circulated through the system via a high-flow pump (model TMFR1, Fluid-O-Tech) that can provide variable flow-rates between 5 and 15 cm-s$^{-1}$. The RO system can operate at pressures between 690-1380 KPa (100-200 psi).

The flat-sheet cell was fabricated from polycarbonate, and it is closed with two 12-mm-thick aluminum plates. The rectangular flow channel (0.077-m wide by 0.002-m thick) has a cross-sectional area of 1.54×10-4 m$^2$. A double "O-ring" arrangement provides a leak-proof seal at the required pressures. Permeate collection is divided into five separate individual sections and corresponding collection ports in order to obtain local permeate flow-rate values at different locations along the flow axis. The length of each port is 0.091 m, so the active permeation area of each port is 7.007×10$^{-3}$ m$^2$. The permeate flow-rate from each of these collection ports (labeled as 1 through 5 where 1 is upstream in the forward-flow direction) is obtained from mass measurements using a balance (model TE2101, Sartorius) with a resolution of 0.1 g. Permeate collection occurs sequentially from each port, and flow from the port to the collection vessel is controlled by five three-way solenoid valves (model 8320G041, ASCO), one on each permeate line. When the solenoid valve is open, the permeate flows to the vessel placed directly on the balance. The valve is opened for a total of 5 min until the next valve opens. When the valve is closed, the permeate flows directly back to the feed tank. The permeate solution from the vessel drains to the feed tank through a siphon. The balance is connected via a RS-232 cable to a laboratory PC.

For pressure regulation, two pressure gauges (only one is shown in FIG. 9) are installed before and after the flow cell to monitor the pressure drop across the cell. A back-pressure regulator (model BP-3-1A1115J111, Go Regulate) is located at the outlet of the flow cell for maintaining the pressure in a flow loop. A pressure sensor (model PX309-300 G-5V, Omega) is located after the first pressure gauge and before the flow cell. A flow sensor (model 101-8E, McMillan Co.) is located on the retentate line on the outlet of the flow cell, and both a pressure sensor and a flow sensor are connected to a 12-bit multifunction I/O analog-to-digital converter (NI-USB 6008, National Instruments). A custom LabVIEW program (Version 8.5., National Instruments) is used to automatically record pressure and retentate flow every 2 min, and mass measurements from the balance every 30 sec; real-time retentate flow-rates, pressure and mass measurements are recorded via a laboratory PC.

Three 10-MHz planar ultrasonic sensors (labeled as A, B and C) in a 1.27-cm diameter element (model V111, Panametrics) are mounted on ports 1, 3 and 5 for continuous monitoring of the acoustic signals. An ultrasonic pulser/receiver (model 505PRX, Panametrics) in conjunction with the ultrasonic sensors and a digital storage oscilloscope (model TDS3052, Tektronix) is used to process and archive real-time acoustic spectra. A multi-channel scanner is used for acquiring the responses from the ultrasonic sensors; the sampling area corresponding to each sensor is about 8 mm$^2$. A second custom LabVIEW program is used to obtain composite ultrasonic spectra from the three sensors every 5 or 10 min (depending on the experiment). The conductivity of the feed and permeate is monitored with a conductivity meter (model 21118537, Fisher Scientific). Membrane salt rejection based on conductivity data during all of the experiments was in the range 97-99%.

Two three-way valves (SV1 and SV3) and one two-way by-pass valve (SV2) are used to ensure that the system can be operated with forward- and reverse-flow. For forward flow, the feed solution is initially delivered from the left end to the right side of the flow cell by opening valve SV1 to the right position and valve SV3 to the down position (dashed line in FIG. 1 referenced by FF). When switching to reverse flow (feed solution enters the flow cell from the right and exits from the left), valve SV2 is opened and valve SV1 is set to the up position and valve SV3 to the left position (dashed line in FIG. 1 referenced by RF).

The membrane used in the experiments is XLE-440 (Filmtec), a polyamide-based extra-low energy RO membrane. The membrane was received from the manufacturer in roll form. Before testing, membrane coupons of the appropriate size (510×110 mm) were sectioned from the roll and then soaked in a 70% aqueous isopropanol solution for 20 min, followed by soaking in ultrapure DI water prior to testing. During this wetting procedure, the container used to soak the membrane was covered with aluminum foil to prevent membrane exposure to light.

Prior to the start of each experiment, the RO system was flushed with ultrapure DI water for 2-3 hours to ensure that the system is clean. Permeate flow-rate data were collected only for ports 1, 3, and 5 (corresponding to ultrasonic sensors A, B, and C, respectively) in order to control the size of the data files. The permeate through ports 2 and 4 was recycled directly into the feed tank; permeate from ports 1, 3 and 5 was also recycled to feed tank. Before each test, the salt solution feed was filtered for 2 hr using an in-line prefilter.

Initial experiments were performed using calcium sulfate solution with concentrations in the range of 0.6-1.0 gL$^{-1}$. After consideration of multiple factors including data size requirements, minimum incubation time and maximum operating time for a full four-cycle test, a calcium sulfate concentration of 0.65 gL$^{-1}$ was chosen for all subsequent experiments. All experiments described in this example utilize this optimum value.

At the completion of each experiment, membrane coupons with an area of 6.5 cm$^2$ are cut from the membrane just beneath the location of ultrasonic sensors A, B and C. Post-mortem characterization included both gravimetric measurements and image analysis. Gravimetric measurements are obtained by comparing the mass of a test coupon to that of a virgin membrane coupon used as a reference. Results are expressed in terms of percent mass change (Δm %). The membrane coupons are also examined via low-magnification light microscopy (20×) and representative images of the membrane coupons surfaces are obtained. Commercial image analysis software (Image J, NIH) is used to analyze the microscopic images by calculating the area coverage (ΔA %) that corresponds to the membrane area directly sampled by the ultrasonic sensor.

In some experiments, energy dispersive spectroscopy (EDS) (NSS, Thermo Scientific) is utilized to confirm the absence or presence of scalant on the membrane coupons. Calcium is used as a marker in both the area mapping as well as total mass modes.

In order to obtain a firm basis for selecting the flow cell operating parameters, a numerical model was utilized for predicting the supersaturation index (SI) and the solute mass-transfer coefficient as a function of system inputs including pressure, bulk solute concentration and inlet flow-rates. A simple film transport model (Graetz mass-transfer correlation) was applied to a parallel plate channel in which the channel height is used as the characteristic flow-channel height for calculation of the Sherwood and Reynolds numbers. In accordance with the design of the cell, the flow channel was divided into five consecutive sections extending from the module entrance to exit. The lumped one-dimensional film model was solved using the flux equation; concentration polarization was incorporated via the osmotic pressure difference between the brine feed (at the wall) and the permeate.

Figure 10:
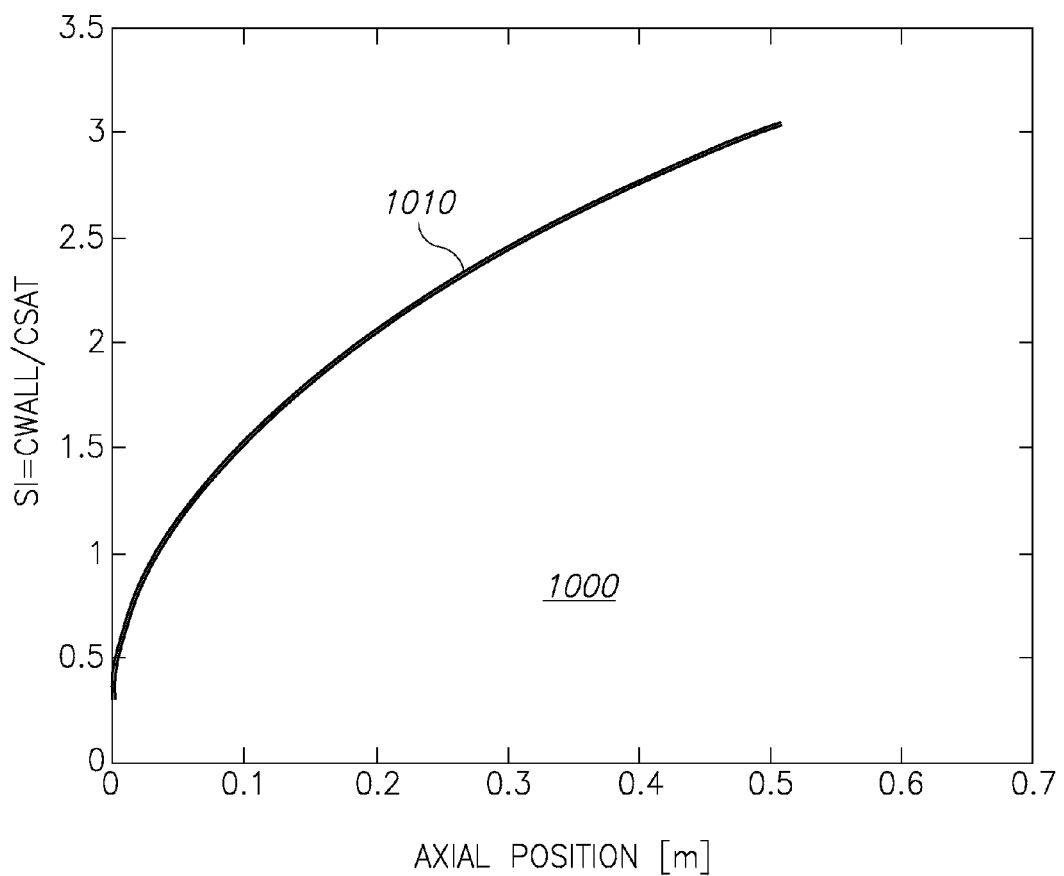
FIGS. 10-23 are graph diagrams illustrating various experimental aspects according to some embodiments of the invention.

The model was employed to determine a combination of concentration, flow velocity and pressure conditions that would enable undersaturation conditions on port 1 (SI~1), and supersaturation (SI~2.5-3) on port 5. As indicated from the modeling results shown in graph 1000 in FIG. 10, these SI values were predicted (line 1010) to occur with a calcium sulfate feed concentration of 0.65 $\mu L^{-1}$ (conductivity: 890±99 $\mu Scm^{-2}$), a pressure of 758±21 kPa (110±3 psi), and a feed flow-rate of 500 mL min$^{-1}$, which corresponds to a cross-flow velocity of 5.4 cm s$^{-1}$. This feed concentration was chosen to best balance an adequate incubation time with a reasonable experimental timescale. The permeate flow-rate decrease due to osmotic pressure changes as the result of the switch from DI water to the 0.65 gL$^{-1}$ feed solution is also predicted using this model. Predicted permeate flow-rate decreases due to osmotic pressure are as follows: 13% (Port 1), 26% (Port 3), and 32% (Port 5).

The experiments conducted enabled the inventors to determine the sensitivity of the externally-mounted ultrasonic sensors in detecting and monitoring early-stage scaling and further enabled to firmly establish proof-of-concept for the methodology. In each test, DI water was initially utilized as the feed solution for at least 48 hr to complete membrane compaction. During the DI water phase, the permeate flow-rate decreased by 20-30% due to membrane compaction. Immediately after the switch from DI water to salt solution, the permeate flow-rate in each ports further deceased by 10-30% initially due to the change of osmotic pressure. During each individual flow cycle, the net permeate flow-rate decreased due to scaling only or increased due to (partial) cleaning of the scalant. The overall permeate flow-rate, which is summation of the flow-rates from three selected ports (1, 3 and 5), is presented as the membrane module performance function, SUM.

Figure 4:
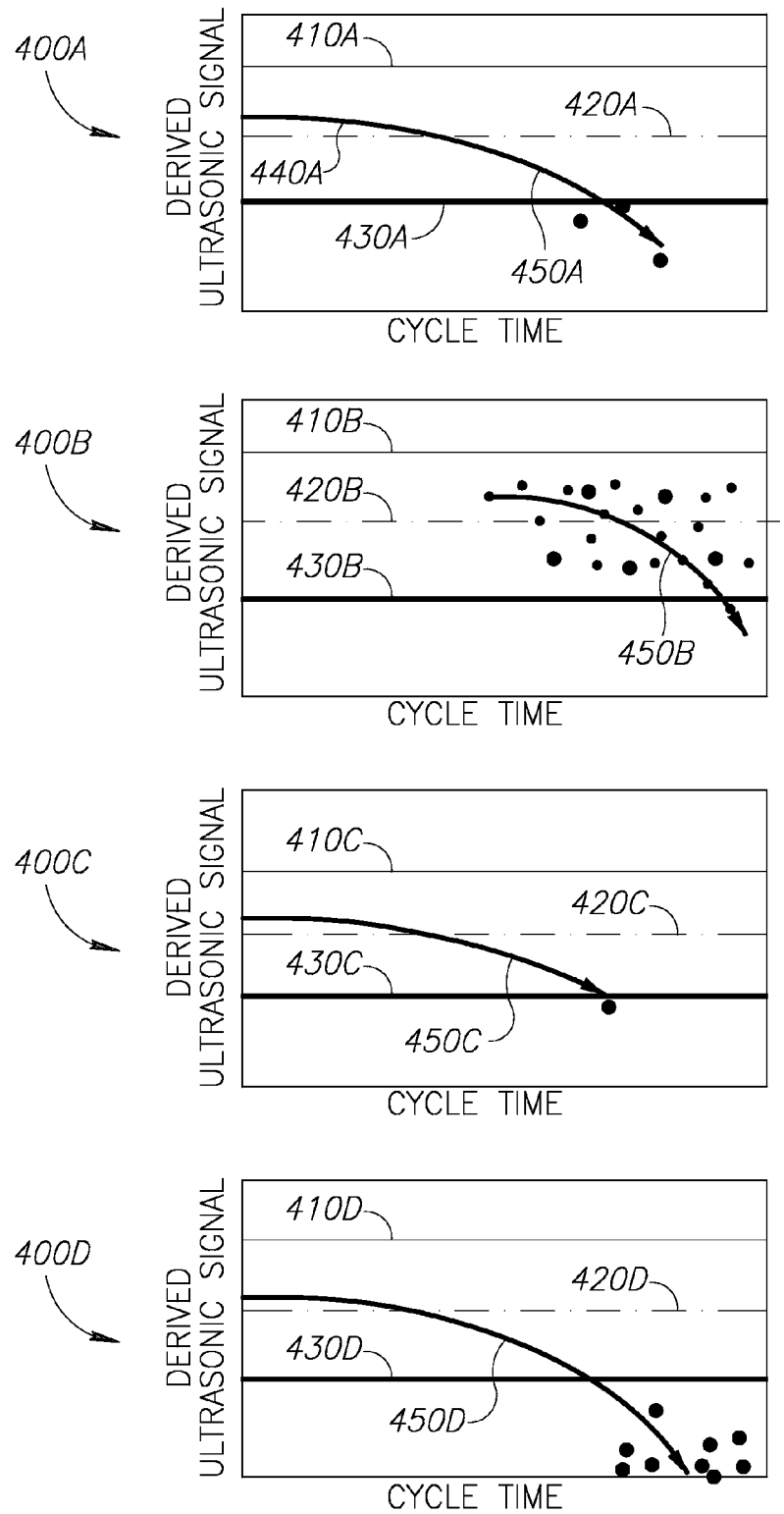
FIG. 4 is a graph illustrating an aspect according to some embodiments of the invention.

A total of four tests were performed. Tests 1-3 were operated in automatic switching mode with a slight modification of the dynamic window methodology. In Test 1, the change in flow direction was triggered after a departure of the trend line from the dynamic window and confirmation by three subsequent contiguous ultrasonic data points that also were outside of the window boundary ("multiple departure" switch, MD) (FIG. 4, graph 400A). In Test 2 the change in flow direction was triggered immediately once the trend line was out of the dynamic window boundary ("first departure" switch, FD) (FIG. 4, graph 400B). Test 3 was conducted via a dynamic window that used only the initial portion of the cycle and a trend line based upon ultrasonic points in the final portion cycle ("modified first departure" switch, MFD): here only the first 30 amplitude points were used to constitute the window boundaries that remained unchanged over the duration of the test, while the trend line was formed using only the 30 last amplitude points of the current cycle (FIG. 4, graph 400C). Test 4 is a reference test with no flow reversal (no-switch test, NS) (FIG. 4, graph 400D). The test results including the total salt phase duration, total number of FF and RF cycles, permeate flow-rate decrease in each port, net permeate flow-rate decrease for entire module (SUM), and post-mortem gravimetric and area coverage analysis are presented in Table 1.

In Test 1, immediately following introduction of the salt solution, the permeate flow-rate decreased 6, 12, and 13% at ports 1, 3, and 5, respectively, due to osmotic pressure changes. Test 1 was operated for 78 hr in the salt solution phase with 7 forward flow (FF) and 6 reverse flow (RF) cycles. The permeate flow-rate decreased by an additional 25, 17, and 17% at ports 1, 3 and 5, respectively, and the overall permeate flow-rate decreased by 24% during the salt solution phase. Results obtained from the ultrasonic sensors, as well as the permeate flow-rate data, were confirmed by post-mortem membrane analysis. The image analysis indicated that no scaling had occurred at port 1, whereas 9 and 16% coverage of the membrane area was observed at ports 3 and 5, respectively (Table 1 above). In addition, negligible mass change was observed on membrane coupons from the respective ports.

The significant permeate flow-rate decrease and high-scaling area coverage at the downstream locations indicated that the methodology used in Test 1 was not as effective as possible in preventing scaling. Therefore, Test 2 was performed using the first departure switch algorithm (FIG. 4, graph 400B). The salt phase in Test 1 lasted 78.5 hr with 17 FF and 17 RF cycles. The permeate flow-rate initially decreased 12, 16 and 20% at ports 1, 3, and 5, respectively, due to osmotic pressure changes, and an additional 6, 5 and 10%, respectively, during the salt phase; these individual responses resulted in an overall permeate flow-rate decrease of 7%. The experiment was terminated at a RF cycle in which port 1 was the downstream port. The membrane area coverage at this port was 7%, while no scaling was detected at ports 3 and 5 (Table 1). In addition, no mass change was observed on membrane coupons from the respective ports. In comparison with Test 1, Test 2 had ~2.5 times more flow cycles over the same duration, and the overall permeate flow-rate decrease was less than one-third that observed in Test 1.

The successful application of the automatic flow-direction switch in the first two tests, which led to a low permeate flow-rate decrease and slight scaling area coverage in Test 2, further verified the effectiveness of the ultrasonic sensors in detecting early-stage scaling during FR and the effectiveness of FR in mitigating scaling. However, the cycle duration significantly varied from 50 min to more than 1000 min. We believe that the variability reflected a few very long cycles in each test, which contributed significantly to the somewhat more extensive surface scaling and greater permeate flow-rate decrease than expected. Thus, the sensitivity of the approach was carefully considered and the dynamic window methodology was modified to differentially weight different portions of each cycle (FIG. 4, graph 400C).

Figure 11:
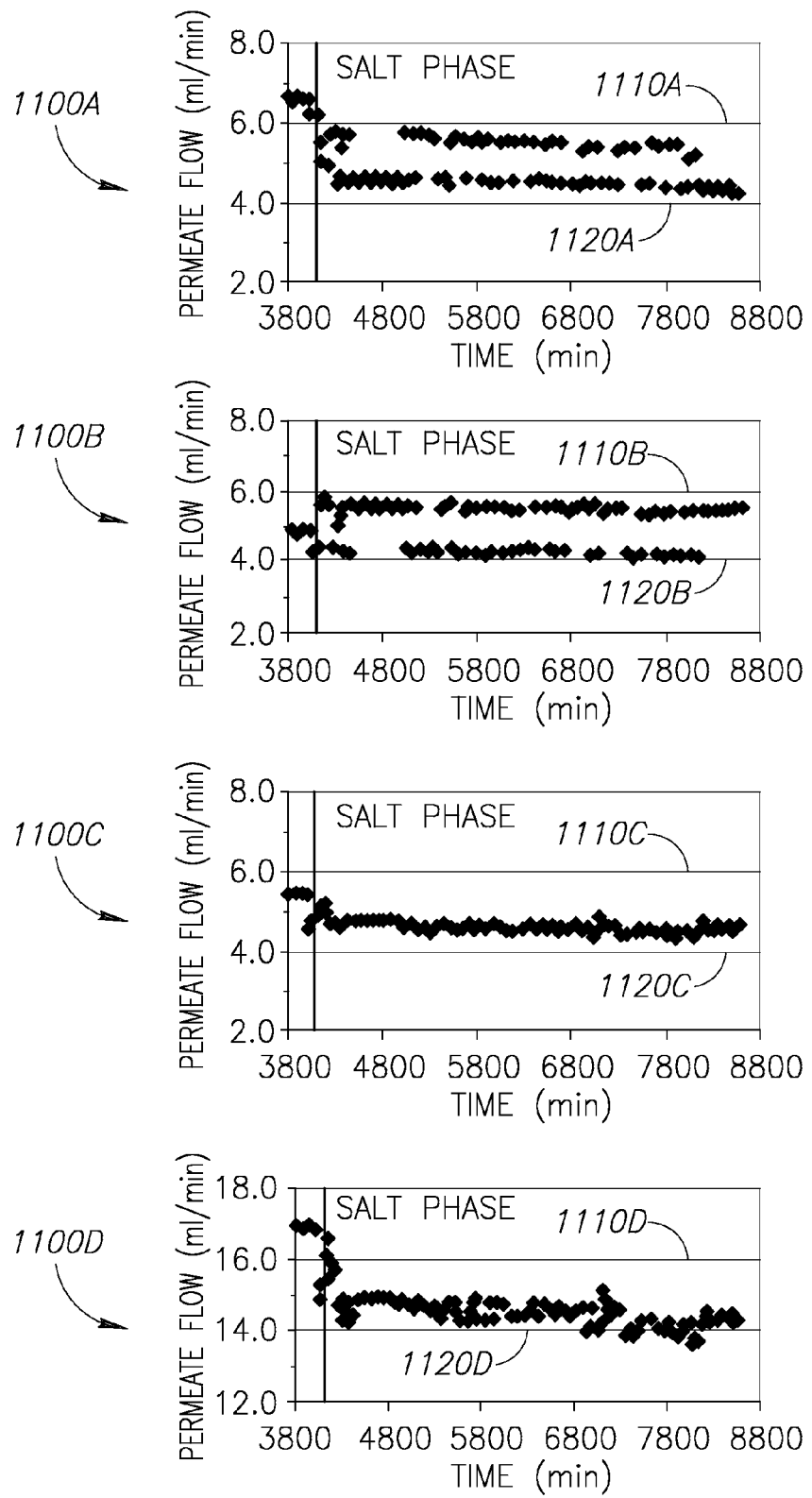
Figure 12:
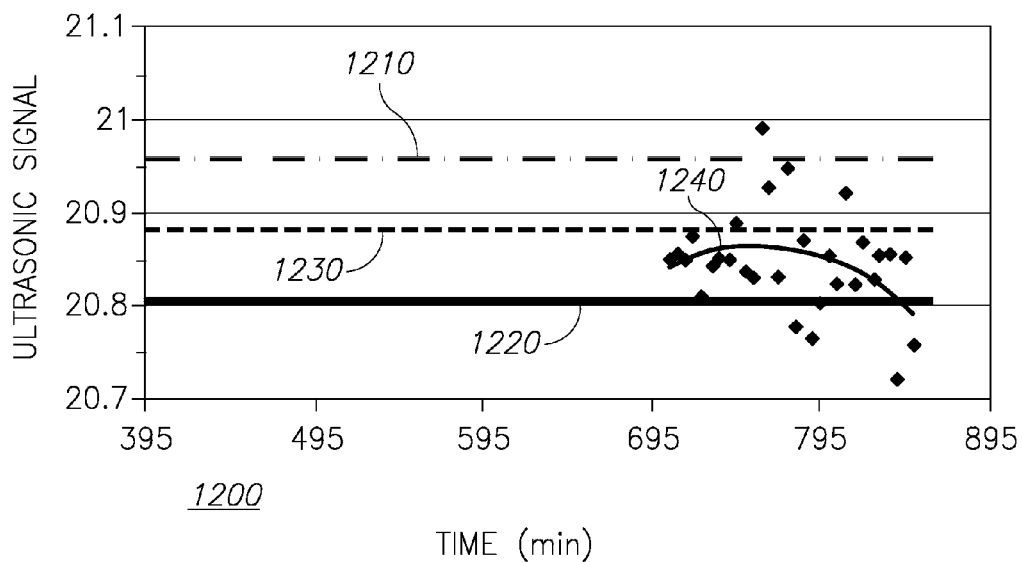

Test 3 was 75.6 hr in duration with 19 FF and 19 RF cycles. The permeate flow-rate decreased 8, 4, and 5% at ports 1, 3, and 5, respectively, resulting in an overall permeate flow-rate decrease of 4% (Table 1). The total permeate flow-rate as well as that for each individual port are presented in FIG. 11: port 1 is presented in 1100A; port 3 is presented in 1100C; port 5 is presented in 1100B; and overall is presented in 1110D. A representative dynamic window result for one of the flow cycles during this test methodology is shown in FIG. 12. The post-mortem gravimetric and image analysis results showed no scaling at ports 1 and 3, and only trace amounts of scaling on the downstream port (port 5). The slight scaling on the membrane surface was hard to detect with light microscopy at a magnification of 20×. Therefore, SEM was used to confirm the presence of scaling in which the size of the precipitate crystals was significantly smaller than those in Test 1. EDS results at port 5 (1.1% wt of calcium) suggested that the ultrasonic sensor is indeed sensitive to different scalant morphologies/sizes on the membrane surface. In addition, the duration of the longest cycle was 460 min. In comparison with the Tests 1 and 2 in which the mean cycle time and standard deviation are 360±366 min and 138±176 min, respectively, the new modified methodology has a mean cycle time and standard deviation of 119±107 min, which clearly reflect a lower level of cycle duration variability.

Test 4 was designed as a reference test for the sensor-controlled automatic FR using a dynamic window methodology. Using the same testing condition as in Tests 1-3, Test 4 was conducted without FR. The test was conducted with a ~77 hr salt phase using a single FF cycle. With the approximately same test duration as of Tests 2 and 3, the permeate flow-rate at the downstream port decreased by 55% and the overall permeate flow-rate decreased by 31%. The interpretation of the results from the ultrasonic sensors and permeate flow-rate data was confirmed by post-mortem light microscopy of the membrane surface and gravimetric analysis of the membrane coupons at the three permeation ports. Gravimetric measurements yielded a mass change of 0, 9, and 8% at ports 1, 3, and 5, respectively, and the image analysis indicated no scaling at port 1 and significant scaling at ports 3 and 5 (Table 1).

Figure 13:
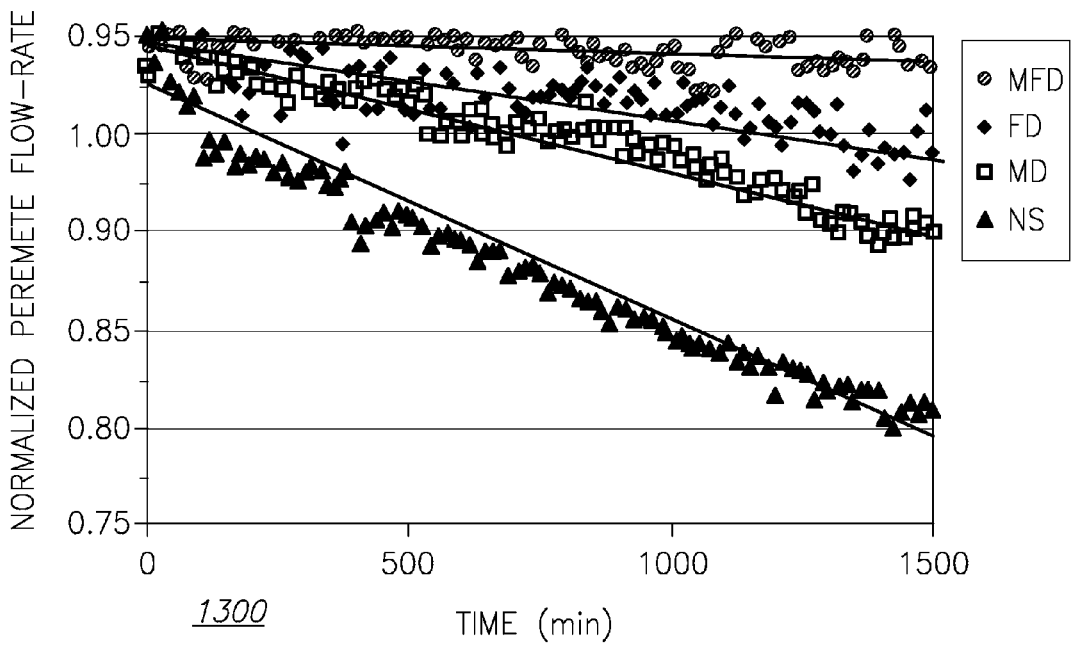

The overall permeate flow-rate decreased only slightly (4-8%) in Test 3 over the ~80-hr experiments, which contained more than 30 FF and RF cycles, when compared to the much greater decline (31%) over the similar test duration of the tests not using FR. Post-mortem analysis in Test 3 indicated that the ultrasonic sensor responded to slight scaling on the downstream port while the midstream and upstream ports were kept free of measureable scalant. In Test 4 under identical operating conditions as in Tests 1-3 but during which FR was not employed, the scaling was extensive and even extended beyond the midstream port. Overall, data from Test 1-3 confirmed that ultrasonically-controlled FR can effectively delay the onset of scaling and improve filtration performance as compared to the case without FR (see FIG. 13).

Table 1 below illustrates a summary of the results from Tests 1-4 showing the total salt phase duration, total number of FF and RF cycles, net permeate flow-rate decrease in each port and all sample ports (SUM), and post-mortem metrics: mass and area coverage.

| Test # | Salt Phase Test Duration (hr) | Total FF and RF Cycles | Last Cycle | Net Permeate Decrease in Each Port (%) | SUM (1 + 3 + 5) Total Permeate Decrease (%) | Δm (%) | ΔA (%) |
|---|---|---|---|---|---|---|---|
| 1 | 78.0 | 7 FF<br>6 RF | FF | 25 (Port 1)<br>17 (Port 3)<br>17 (Port 5) | 24 | 0 (Port 1)<br><1 (Port 3)<br>0 (Port 5) | 0 (Port 1)<br>9 (Port 3)<br>16 (Port 5) |
| 2 | 78.5 | 17 FF<br>17 RF | RF | 6 (Port 1)<br>5 (Port 3)<br>10 (Port 5) | 7 | 0 (Port 1)<br>0 (Port 3)<br>0 (Port 5) | 7 (Port 1)<br>0 (Port 3)<br>0 (Port 5) |
| 3 | 75.6 | 19 FF<br>19 RF | FF | 8 (Port 1)<br>4 (Port 3)<br>5 (Port 5) | 4 | 0 (Port 1)<br>0 (Port 3)<br>0 (Port 5) | 0 (Port 1)<br>0 (Port 3)<br><1 (Port 5) |
| 4 | 76.6 | 1 FF | FF | 5 (Port 1)<br>35 (Port 3)<br>55 (Port 5) | 31 | 0 (Port 1)<br>9 (Port 3)<br>8 (Port 5) | 0 (Port 1)<br>58 (Port 3)<br>65 (Port 5) |

EXAMPLE 2

The apparatus is the same in example 1 except the pulser/receiver is a Olympus model 5072pr, the multiplexer used is MUX-8 (Simex Systems Be-Insp), the reflected waveforms are stored by a Tektronix TDS3012C digital oscilloscope from which they are fed to the computer. The A/D interface for weight, temperature, pressures and reflected waveforms is a National Instruments NI-9219 card connected to a PC. The process and waveform input data is analyzed by software written on the LabVIEW platform (version 8.5) which generates the average amplitude, trend line and standard deviation window as described in the patent and in FIG. 4. The LabVIEW written software then sends signals via the USB 6008 D/A card to the valves to effect when the trend line intersects the operation window which is held at +/−1 to 1.2 times the standard deviation of the average amplitude. Intersections in the first 15 minutes of each cycle are ignored since they reflect the noisiness of the initial data.

The scaling system was a solution of 1 g/L of calcium sulfate dihydrate with a flow rate of 90 L/min and an average applied pressure of 9.5 bar. The membrane permeability was 7.35 L/m$^2$·h.

Figure 14:
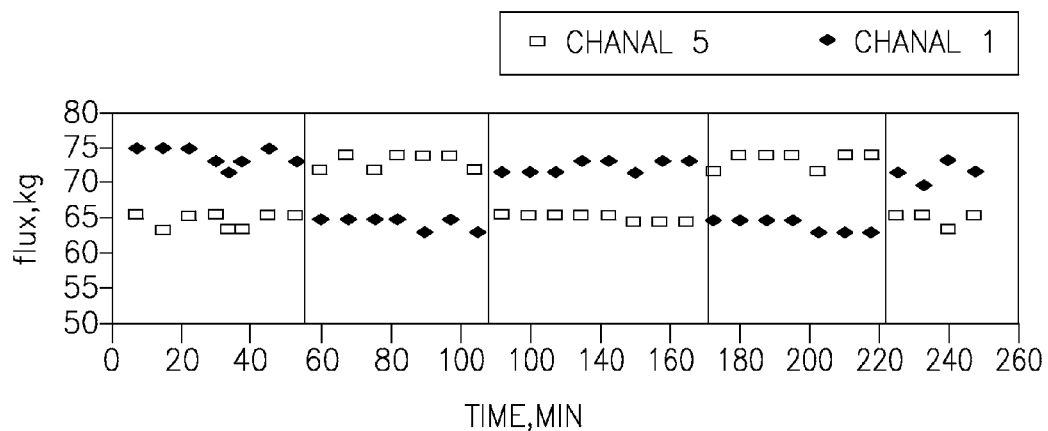
Figure 15:
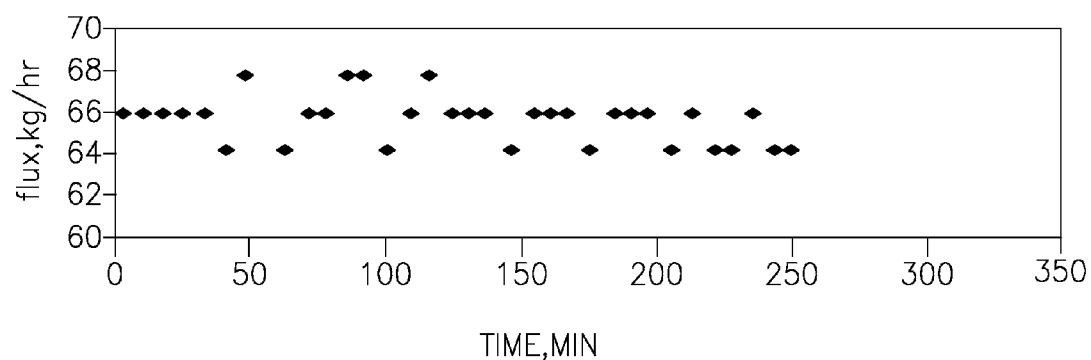
Figure 16:
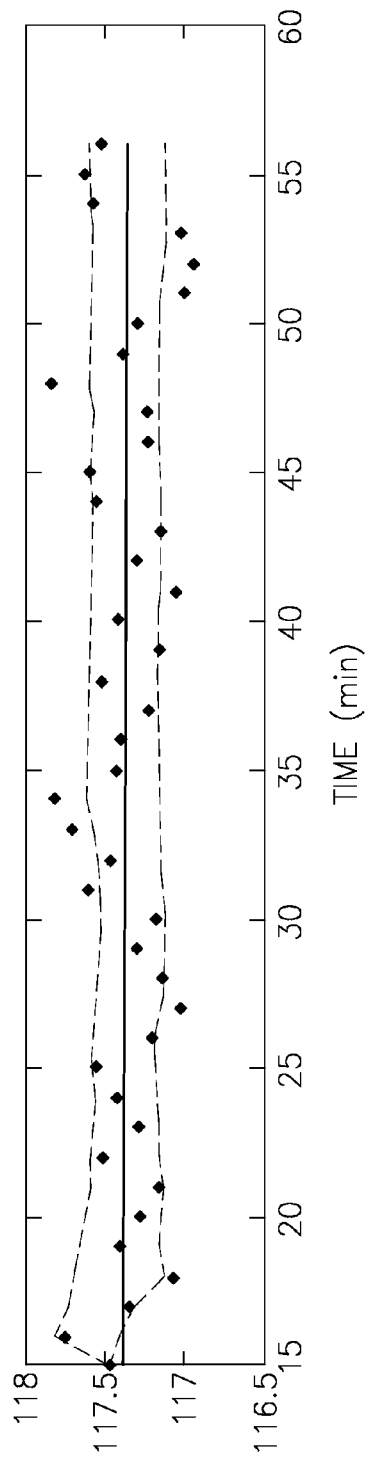
Figure 17:
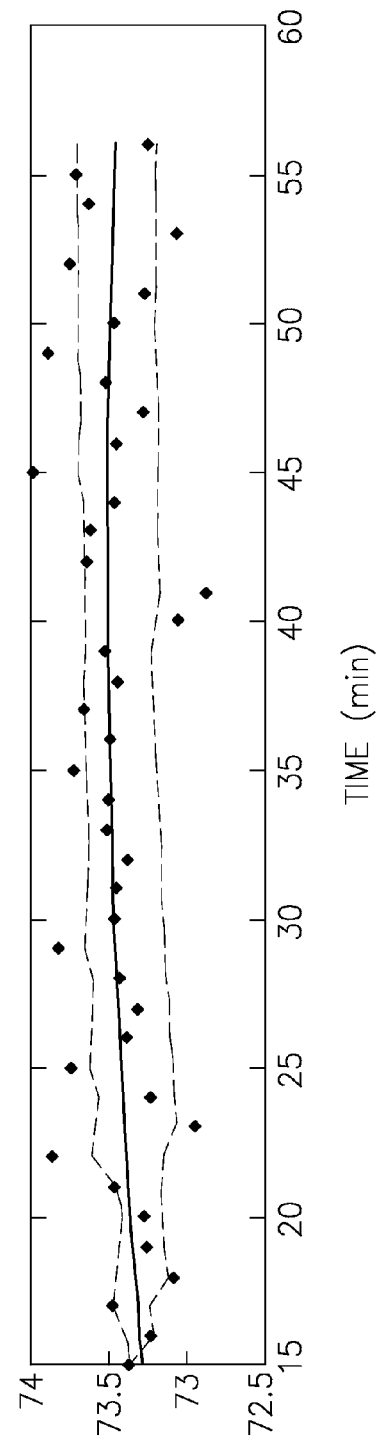
Figure 18:
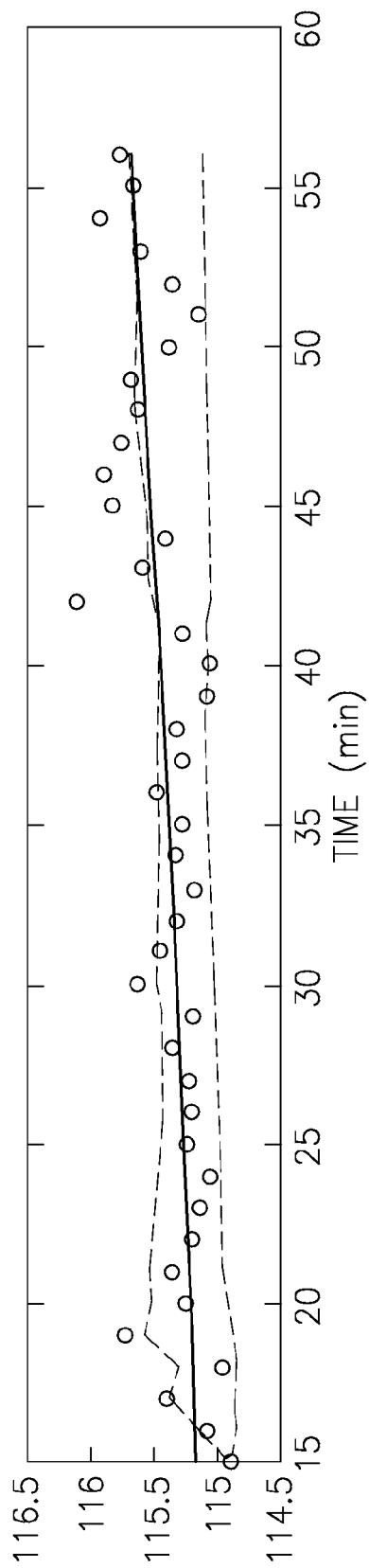

The results of operating for 250 minutes are shown in FIGS. 14 and 15. As can be seen the intervention is successful in preventing flux decline. From the plots of the ultrasonic signal it was seen that the intersection is sometimes with the lower limit and sometimes with the upper limit. The induction times were on the same order of magnitude 55-65 minutes with variation expected by the random uncertainty and the fact that the nucleation will not always take place first under the area sampled by the ultrasonic sensor. However the sensitivity is great enough that the flux is maintained constant. In FIGS. 16-18, the plots of the ultrasonic signals for all three sensors are displayed for the first cycle with calculated trendline displayed at the time of the first switch. It can be seen that the trendline cross the window boundary only for the downstream most sensor shown in FIG. 18. This confirms that the sensor is adequately sensitive to cause the switch before further upstream sections are scaled. On the last cycle, the experiment was stopped without switching and the cell was opened. The results for the ultrasonic signal further show that the upstream sensors for channels 1 and 3 did not leave the window, but the signal from the downstream sensor for channel 5 did just leave the window at 57 minutes. There is only just beginning a flux decline which is barely discernible after 65 minutes. The micrographs of the membrane in the fifth channel and the surface coverage under the area sampled by the ultrasonic sensor was less than 1%, yet the deposit was detected whereas no deposit was discernible in the areas under the two upstream sensors.

EXAMPLE 3

Successful Detection of Threshold Scaling with Calcium Carbonate

The same apparatus was used as in example 2. However the feed solution was composed of 7 mM $CaCl_2$ and 7 mM $NaHCO_3$. The feed pH was adjusted by bubbling $CO_2$ into the feed tank and was maintained by a pH controller that determined the frequency of opening and closing a solenoid leading from the $CO_2$ gas cylinder to an injection pipe in the feedline. For this experiment the feed pH was maintained at 6.8. Given the equilibrium constants and calculating the concentration polarization as described in example 1, but allowing for the lower rejection of carbonic acid (73%) as opposed to calcium chloride (100%) and sodium bicarbonate (~98%) based on the hydrodynamic conditions, it was possible to calculate the calcite supersaturation at the membrane wall as a function of downstream distance from the port entrance. Under conditions of 89 L/h recycle rate, pressure of 11 bar and initial flux of ~65 $L/m^2$-h, this results in an average Langelier saturation index (LSI) (=base 10 logarithm of saturation index of calcite) of 0.75 (SI=5.6) in the most upstream port (initially port 1) and average Langelier saturation index of 0.97 (SI=9.4) in the middle permeate port, and an average Langelier saturation index (LSI) of 1.02 (SI=10.4) in the most downstream port (initially port 5). The flow direction was not switched after scaling began in the downstream port until ~30 minutes after the first indication of scaling in the downstream port (5) as seen in the ultrasonic sensor.

Figure 19:
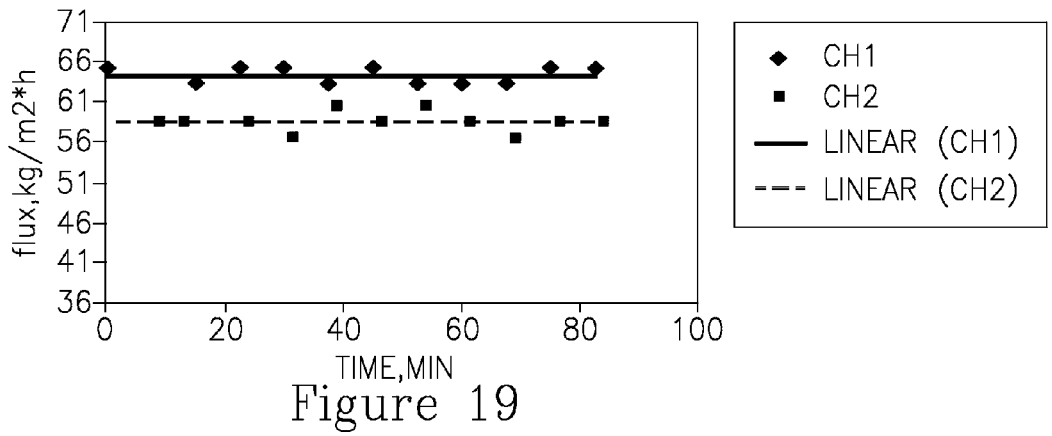
Figure 20:
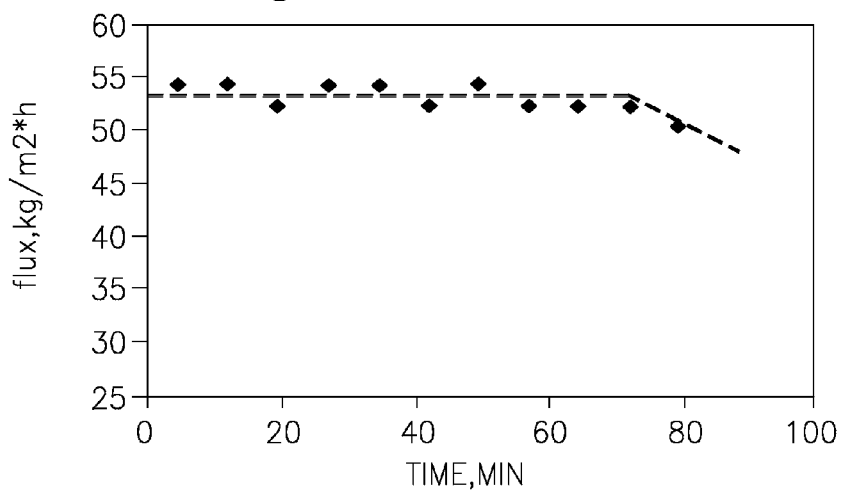
Figure 21:
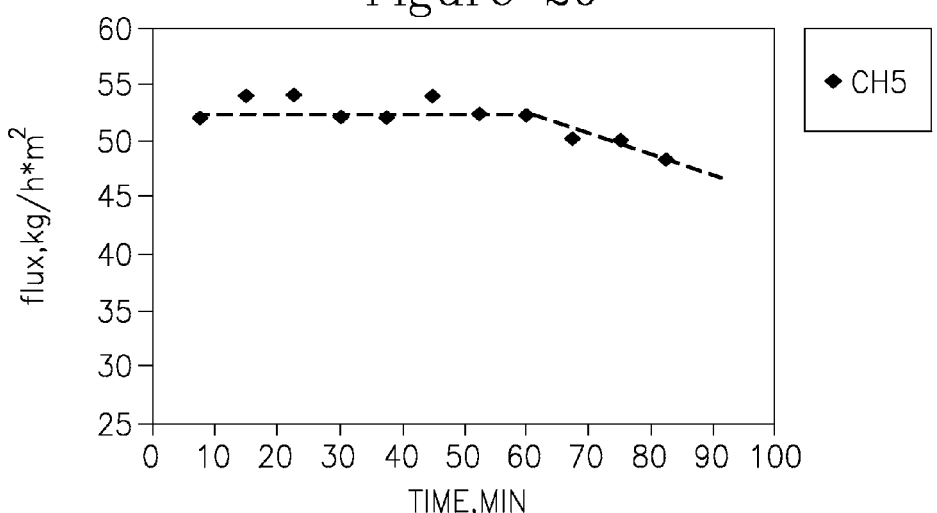
Figure 22:
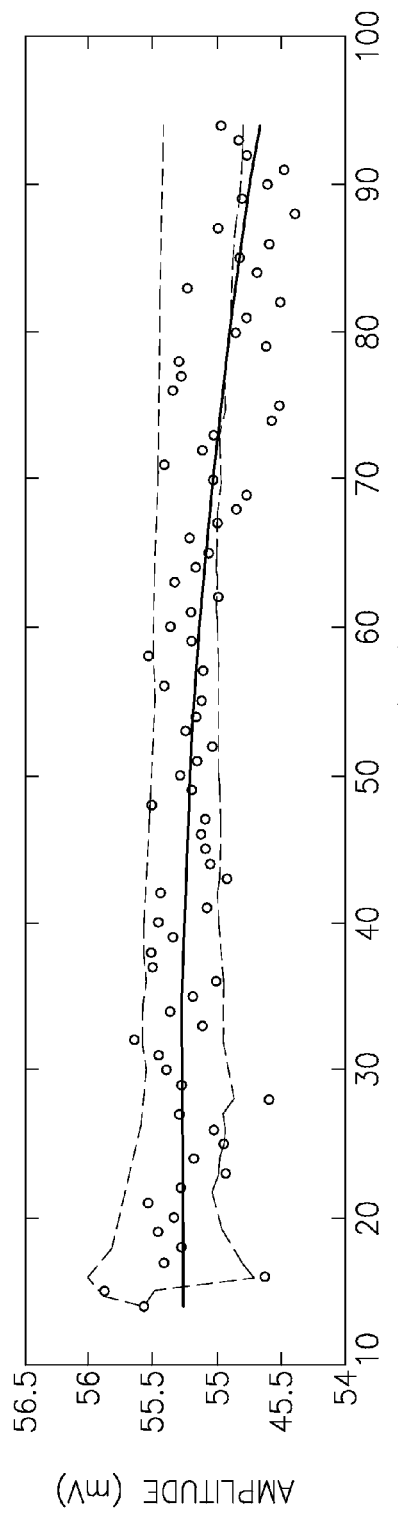
Figure 23:
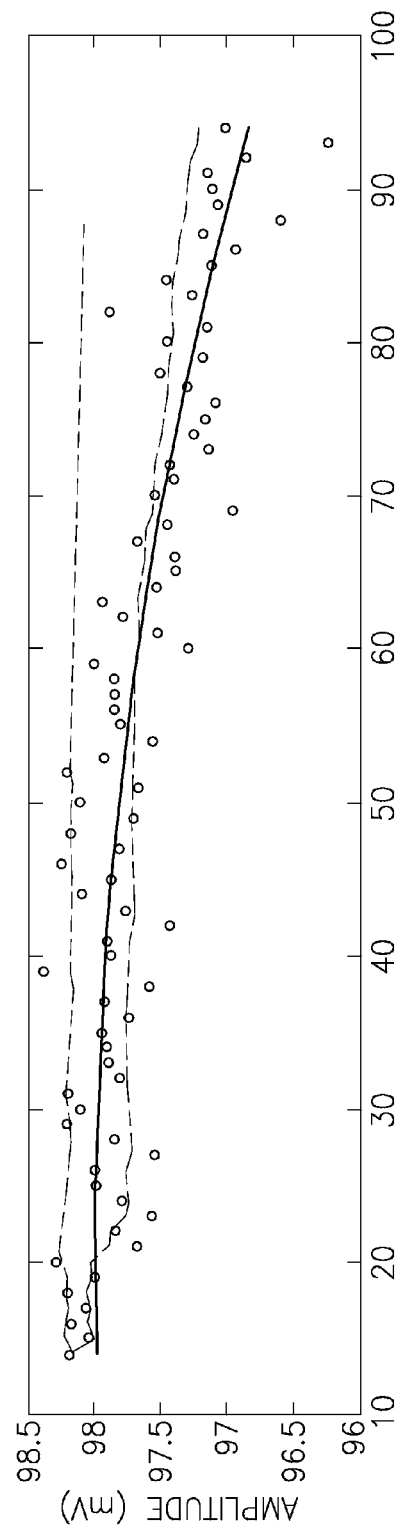

FIGS. 19, 20, and 21 show the fluxes for ports 1,2,3, and 5 respectively. FIG. 20 shows the trend line of the ultrasonic sensor at middle of port 3, and FIGS. 22 and 23 show the trend line from the ultrasound sensor at the upstream end of port 5, which is the most downstream port. As can be seen in FIG. 21, the flux in port 5 begins to decrease at about 63 min whereas the flux in port 3 begins to decrease at about 75 min. In contrast, the flux in ports 1 and 2 are stable. The corresponding ultrasonic response from port 5 shows the ultrasonic signal crossing the window first (about 60 min), followed by sensor from port 3 showing decline at a somewhat later time (about 75 min).

Micrographs of the membrane in port 3 in the area under its ultrasonic sensor and the membrane in port 5 in the area under its ultrasonic sensor were taken. These micrographs show that the amounts of deposit in evidence clearly indicate that the ultrasonic sensor that gave an earlier signal (Port 5) showed more massive deposit given the longer run time after initial ultrasonic indications of scaling. No scale was found on the membrane under the upstream sensor (Port 1).

In a subsequent crossflow experiment under the same composition and hydrodynamic conditions of crossflow velocity and flux, switching was initiated as soon as the ultrasonic sensor showed signs of scaling in the downstream port (Sensor 3 on port 5). In this case no signs of scaling had yet been found by the ultrasonic sensor in the upstream ports (sensors 1 and 2) whereas the supersaturation was not as high as in port 5 (sensor 3).

While the invention has been described with respect to a limited number of embodiments, these should not be construed as limitations on the scope of the invention, but rather as exemplifications of some of the preferred embodiments. Other possible variations, modifications, and applications are also within the scope of the invention.

The invention claimed is:

1. A method of detecting pre-conditions of scaling occurring on internal surfaces of conduits of water processing equipment, the method comprising:
    transmitting one or more ultrasonic signals through the wall of the conduits;
    deriving, in real-time, data samples indicative of spectral parameters, from received ultrasonic signals or reflections thereof;
    calculating a moving average of a scatter of the ultrasonic signals, over a specified period of time, based on the data samples;
    applying a statistical operand to the moving average, to yield a statistical distribution metric;
    determining a dynamic window defined by: (i) an upper boundary being the moving average plus at least a fraction of the statistical distribution metric and (ii) a lower boundary being the moving average minus the at least a fraction of the statistical distribution metric;
    generating a trend line being a fitting of the derived samples and
    monitoring the trend line within the dynamic window to detect a crossover of the trend line at the upper boundary or the lower boundary.

2. The method according to claim 1, further comprising dynamically updating the values of the upper boundary and the lower boundary in real-time.

3. The method according to claim 2, wherein the updating is carried out at least partially in order to compensate for temperature changes over time affecting the ultrasonic signals.

4. The method according to claim 1, wherein the upper and lower boundaries are adjusted during an initial period of time and then remain fixed.

5. The method according to claim 1, wherein the specified period of time starts at t=0 and ends at initial sampling time $t_1$ or starts at t−Δt and ends at time t being a current time.

6. The method according to claim 1, wherein the generated trend line, the upper and the lower boundaries represent an estimation of future values respectively, and wherein the monitoring is carried out in order to detect conditions at time t+Δt at which a specified action would occur wherein t being a current time.

7. The method according to claim 1, wherein the statistical distribution metric is a variance or a standard deviation.

8. The method according to claim 1, wherein the fitting is a second degree polynomial regression line that yields a specified function.

9. The method according to claim 1, further comprising issuing an alert upon the detection of a crossover.

10. The method according to claim 1, further comprising applying an intervention in the water processing equipment such that the scaling is avoided.

11. The method according to claim 10, wherein the intervention comprises at least one of: flow reversal, flushing with undersaturated water, osmotic flushing, and a use of a chemical cleaning solution.

12. The method according to claim 1, wherein the water processing equipment comprises at least one of: reverse osmosis, nanofiltration, ultrafiltration membranes, heat exchangers, and water transport pipelines.

13. The method according to claim 1, wherein the spectral parameters include at least one of: amplitude, phase, and combinations and derived functions thereof.

14. The method according to claim 1, wherein the scaling occurs due to at least one of the following minerals: calcium carbonate, calcium sulfate, calcium fluoride, calcium phosphate, barium sulfate, strontium sulfate, zirconia, and silica.

15. A system for detecting pre-conditions of scaling occurring on internal surfaces of conduits of water processing equipment, the system comprising:
- at least one ultrasonic transceiver configured to: (i) transmit one or more ultrasonic signals through the wall of the conduits, and (ii) receive the ultrasonic signals and reflections thereof;
- a sampler configured to sample and derive, in real-time, data samples indicative of spectral parameters, from received ultrasonic signals or reflections thereof; and
- a processing unit configured to:
- (vi) calculate a moving average of a scatter of the ultrasonic signals, over a specified period of time, based on the data samples;
- (vii) apply a statistical operand to the moving average, to yield a statistical distribution metric;
- (viii) determine a dynamic window defined by: (i) an upper boundary being the moving average plus at least a fraction of the statistical distribution metric and (ii) a lower boundary being the moving average minus the at least a fraction of the statistical distribution metric;
- (ix) generate a trend line being a fitting of the derived samples; and
- (x) monitor the trend line within the dynamic window to detect a crossover of the trend line at the upper boundary or the lower boundary.

16. The system according to claim 15, wherein the values of the upper boundary and the lower boundary are dynamically updated in real-time.

17. The method according to claim 16, wherein the updating is carried out at least partially in order to compensate for temperature changes over time affecting the ultrasonic signals.

18. The method according to claim 15, wherein the upper and lower boundaries are adjusted during an initial period of time and then remain fixed.

19. The method according to claim 15, wherein the specified period of time starts at $t=0$ and ends at initial sampling time $t_1$ or starts at $t-\Delta t$ and ends at time t being a current time.

20. The method according to claim 15, wherein the generated trend line, the upper and the lower boundaries represent an estimation of future values respectively, and wherein the monitoring is carried out in order to detect conditions at time $t+\Delta t$ at which a specified action would occur wherein t being a current time.

21. The system according to claim 15, wherein the statistical distribution metric is a variance or a standard deviation.

22. The system according to claim 15, wherein the fitting is a second degree polynomial regression line.

23. The system according to claim 15, further comprising a control module configured to issue an alert upon the detection of a crossover.

24. The system according to claim 15, further comprising a control module configured to apply an intervention to the water processing equipment such that the scaling is avoided.

25. The system according to claim 24, wherein the intervention comprises at least one of: flow reversal, flushing with undersaturated water, osmotic flushing, and a use of a chemical cleaning solution.

26. The system according to claim 15, wherein the water processing equipment comprises at least one of: reverse osmosis, nanofiltration, ultrafiltration membranes, heat exchangers, and water transport pipelines.

27. The system according to claim 15, wherein the spectral parameters include at least one of: amplitude, phase, and variance thereof.

28. The method according to claim 15, wherein the scaling occurs due to at least one of the following minerals: calcium carbonate, calcium sulfate, calcium fluoride, calcium phosphate, barium sulfate, strontium sulfate, zirconia, and silica.

* * * * *